US006319497B1

(12) United States Patent
Casida, Jr. et al.

(10) Patent No.: US 6,319,497 B1
(45) Date of Patent: Nov. 20, 2001

(54) **NON-OBLIGATE PREDATORY BACTERIUM *BURKHOLDERIA CASIDAE* AND USES THEREOF**

(75) Inventors: Lester Earl Casida, Jr., State College, PA (US); Joseph Oliver Falkinham, III, Blacksburg, VA (US); Cody Christopher Cain, Decatur, GA (US)

(73) Assignees: Virginia Tech Intellectual Properties, Inc., Blacksburg; Virginia Polytechnic Institute and State University, Blacksburge, both of VA (US); The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/063,898

(22) Filed: Apr. 22, 1998

Related U.S. Application Data
(60) Provisional application No. 60/044,532, filed on Apr. 23, 1997.

(51) Int. Cl.⁷ ..................................................... C12N 1/20
(52) U.S. Cl. ................. 424/93.47; 424/93.4; 435/252.34; 435/874
(58) Field of Search ............................... 424/93.4, 93.47; 435/252.34, 874

(56) References Cited

U.S. PATENT DOCUMENTS

| | | | |
|---|---|---|---|
| 4,588,584 | 5/1986 | Lumsden et al. | 424/93.47 |
| 4,798,723 | 1/1989 | Dart et al. | 424/93.47 |
| 4,988,586 | 1/1991 | Toyoda et al. | 424/93.2 |
| 5,089,263 | 2/1992 | Spiegel et al. | 424/93.47 |
| 5,232,850 | 8/1993 | Casida, Jr. | 435/253.3 |
| 5,244,658 | 9/1993 | Parke | 504/117 |
| 5,264,210 | 11/1993 | Novitski et al. | 424/93.47 |
| 5,288,633 | 2/1994 | Cartwright et al. | 435/253.3 |
| 5,348,742 | 9/1994 | Howell et al. | 424/93.47 |
| 5,360,606 | 11/1994 | Parke et al. | 424/93.47 |
| 5,413,783 | 5/1995 | McLaughlin et al. | 424/93.51 |
| 5,496,547 | 3/1996 | Lam et al. | 424/93.47 |
| 5,552,315 | 9/1996 | Slininger et al. | 435/253.3 |
| 5,554,368 | 9/1996 | Stack et al. | 424/93.47 |
| 5,576,298 | 11/1996 | Strobel et al. | 514/15 |

FOREIGN PATENT DOCUMENTS

| | | |
|---|---|---|
| 7-255486 A1 | 10/1995 | (JP) . |
| WO 95/11310 | 4/1995 | (WO) . |

OTHER PUBLICATIONS

Anderson & Liberta, 1986, "Occurrence of fungal–inhibiting *Pseudomonas* on caryopses of *Tripsacum dactyloides* L. and its implication for seed survival and agriculture application", *Journal of Applied Bacteriology* 61:195–199.

Ballard et al., 1970, "Taxonomy of the aerobic pseudomonads: *Pseudomonads cepacia*, *P. marginata*, *P. alliicola* and *P. caryophylli*", *J. Gen. Microbiol.* 60:199–214.

Bevivino et al., 1994, "Phenotypic comparison between rhizosphere and clinical isolates of *Burkholderia cepacia*", *Microbiology* 140:1069–1077.

L.E. Casida, Jr., 1980, "Death of *Micrococcus luteus* in soil", *Applied and Environ. Microbiol.* 39:1031–1034.

L.E. Casida, Jr., 1980, "Bacterial predators of *Micrococcus luteus* in soil", *Applied and Environ. Microbiol.* 39:1035–1041.

L.E. Casida, Jr., 1982, "*Ensifer adhaerens* gen. nov., sp. nov.: A bacterial predator of bacteria in soil", *Internat'l J. Systematic Bacteriol.* 32:339–345.

L.E. Casida, Jr., 1987, "Relation to copper of N–1, a nonobligate bacterial predator", *Applied and Environ. Microbiol.* 53:1515–1518.

L.E. Casida, Jr., 1988, "Response in soil of *Cupriavidus necator* and other copper–resistant bacterial predators of bacteria of addition of water, soluble nutrients, various bacterial species, or *Bacillus thuringiensis* spores and crystals", *Applied and Environ. Microbiol.* 54:2161–2166.

L.E. Casida, Jr., 1988, "Minireview: Nonobligate bacterial predation of bacteria of soil", *Microb. Ecol.* 15:1–8.

L.E. Casida, Jr., 1989, "Protozoan response to the addition of bacterial predators and other bacteria to soil", *Applied and Environ. Microbiol.* 55:1857–1859.

Casida, Jr. & Lukezic, 1992, "Control of leaf spot diseases of alfalfa and tomato with applications of the bacterial predator *Pseudomonas* strain 679–2", *Plant Dis.* 76:1217–1220.

Goto et al., 1994, "Occurrence and properties of copper–resistance in plant pathogenic bacteria", *Ann. Phytopath. Soc. Japan* 60:147–153.

Hebbar et al., 1992, "*Pseudomonas cepacia*, a potenial suppressor of maize soil–borne diseases—seed inoculation and maize root colonization", *Soil Biol. Biochem.* 24:999–1007.

Hebbar et al., 1992, "Suppression of *Fusarium moniliforme* by maize root–associated *Pseudomonas cepacia*", *Soil Biol. Biochem.* 24:1009–1020.

(List continued on next page.)

Primary Examiner—Jean C. Witz
(74) Attorney, Agent, or Firm—Pennie & Edmonds LLP

(57) ABSTRACT

A novel predator bacterium *Burkholderia casidae* is disclosed. The invention is directed to the isolation and use of *Burkholderia casidae* to control microbial diseases of plants. The genetic, biochemical and physiological characteristics of *Burkholderia casidae* are described. Biocontrol compositions comprising *Burkholderia casidae*, and antimicrobial compounds and antimicrobial preparations prepared from *Burkholderia casidae* are also disclosed, as are methods for accomplishing all of the foregoing.

34 Claims, 1 Drawing Sheet

OTHER PUBLICATIONS

Lee et al., 1994, "Cepacidine A, a novel antifungal antibiotic produced by *Pseudomonas cepacia*", *J. Antibiotics* 47:1402–1405.

Leff et al., 1995, "Identification of aquatic *Burkholderia* (*Pseudomonas*) *cepacia* by hybridization with species–specific rRNA gene probes", *Applied & Environ. Microb.*61:1634–1636.

Makkar & Casida, Jr., 1987, "*Cupriavidus necator* gen. nov., sp. nov.: A nonobligate bacterial predator of bacteria in soil", *Internat'l J. System. Bacteriol.*37:323–326.

McLoughlin et al., 1992, "*Pseudomonas cepacia* suppression of sunflower wilt fungus and role of antifungal compounds in controlling the disease", *Applied & Environ. Microb.*58:1760–1763.

Meyer et al., 1995, "Ornibactin production and transport properties in strains of *Burkholderia vietnamiensis* and *Burkholderia cepacia* (formerly *Pseudomonas cepacia*)", *BioMetals* 8:309–317.

Palleroni & Holmes, 1981, "*Pseudomonas cepacia* sp. nov., nom. rev.", *Internat'l J. Systematic Bacteriol.* 31: 479–481.

Ralston et al., 1973, "*Pseudomonas pickettii*, a new species of clinical origin related to *Pseudomonas solanacearum*", *Internat'l J. Systemic Bacteriol.*23:15–19.

Rodley et al., 1995, "A physical genome map of the *Burkholderia cepacia* type strain", *Mol. Microbiol.*17:57–67.

Rosales et al., 1995, "Isolation and identification of antifungal metabolites produced by rice–associated antagonistic *Pseudomonas* spp.", *Phytopath.*85:1028–1032.

Sánchez et al., 1994, "Inoculated common beans are protected against *Macrophomina phaseolina* by *Burkholderia cepacia* UPR 5C", *Plant and Soil* 162:293–297.

Smilanick & Denis–Arrue, 1992, "Control of green mold of lemons with Pseudomonas species", *Plant Dis.*76:481–485.

Tsuchiya et al., 1995, "Practical detection of *Pseudomonas cepacia* from rhizosphere antagonistic to plant pathogens with a combination of selective medium and ELISA", *Ann. Phytopathol. Soc. Jpn.* 61:318–324.

Urakami et al., 1994, "Transfer of *Pseudomonas plantarii* and *Pseudomonas glumae* to Burkholderia as Burkholderia spp. and description of *Burkholderia vandii* sp. nov.", *Internat'l J. System. Bacteriol.* 44:235–245.

Yabuuchi et al., 1992, "Proposal of Burkholderia gen. nov. and transfer of seven species of the genus Pseudomonas homology group II to the new genus, with the type species *Burkholderia cepacia* (Palleroni and Holmes 1981) comb. nov.", *Microbiol. Immunol.*36:1251–1275.

Zeph & Casida, Jr., 1986, "Gram–negative versus gram–positive (actinomycete) nonobligate bacterial predators of bacteria in soil",*Applied & Environ. Microbiol.*52:819–823.

Gomez–Galue et al., 1996, "Biocontrol of charcoal rot and rhizoctoniasis on common bean by antagonistic strains of *Bacillus cereus* and *Burkholderia cepacia*", *Phytopathology* 86:S114.

Larkin et al., 1996, "Efficacy of various biocontrol organisms in the control of Fusarium wilt of tomato", Phytopathology 86:S83.

Li et al., 1993 "Phylogenetic studies of the rRNA group II pseudomonads based on 16S rRNA gene sequences", *J. Applied Bacteriology* 74:324–329.

Mao et al., 1996, "Effect of temperature on corn seed treatment with biocontrol agents to suppress damping–off", Phytopathology 86:S23.

Tabacchioni et al., 1995, "Molecular characterization of rhizosphere and clinical isolates of *Burkholderia cepacia*", *Res Microbiol.*146:531–542.

Derwent WPI Acc. No. 95–378541/199549 (English Abstract for JP 7–255486 A1).

International Search Report, Patent Cooperatiion Treaty, dated June 29, 1998 issued in connection with PCT/US98/08148 which is an International counterpart to the present application.

```
5'-
AAATATTACG CTGGTTGCAT GCCTTACAGC ATGCAAGTCG AACGGCAGCA CGGGTGCTTG
CACCTGGTGG CGAGTGGCGA ACGGGTGAGT AATACATCGG AACAATGTCC TGTAGTGGGG
GATAGCCCGG CGAAAGCCGG ATTAATACCG CATACGATCT ACGGATGAAA GCGGGGGACC
TTCGGGCCTC GCGCTATAGG GTTGGCCGAT GGCTGATTAG CTAGTTGGTG GGGTAAAGGC
CTACCAAGGC GACGATCAGT AGTTGTCTGA GAGGACGACC AGCCACACTG GGACTGAGAC

ACGGCCCAGA CTCTTACGGG AGGCAGCAGT GGGGAATTTT GGACAATGGG CGAAAGCCTG
ATCCAGCAAT GCCGCGTGTG TGAAGAAGGC CTTCGGGTTG TAAAGCACTT TTGTCCGGAA
AGAAATCCTT GGTTCTAATA TAGCCGGGGG ATGACGGTAC CGGAAGAATA AGCACCGGCT
AACTACGTGC CAGCAGCCGC GGTAATACGT AGGGTGCGAG CGTTAATCGG AATTACTGGG
CGTAAAGCGT GCGCAGGCGG TTTGCTAAGA CCGATGTGAA ATCCCCGGGC TCAACCTGGG

AACTGCATTG GTGACTGGCA GGCTAGAGTA TGGCAGAGGG GGGTAGAATT CCACGTGTAG
CAGTGAAATG CGTAGAGATG TGGAAGAATA CCGATGGCGA AGGCAGCCCC CTGGGCCAAT
ACTGACGCTC ATGCACGAAA GCGTGGGGAG CAAACAGGAT TAGATACCCT GGTAGTCCAC
GCCCTAAACG ATGTCAACTA GTTGTTGGGG ATTCATTTCC TTAGTAACGT AGCTAACGCG
TGAAGTTGAC CGCCTGGGGA GTACGGTCGC AAGATTAAAA CTCAAAGGAA TTGACGGGGA

CCCGCACAAG CGGTGGATGA TGTGGATTAA TTCGATGCAA CGCGAAAAAC CTTACCTACC
CTTGACATGG TCGGAATCCC GCTGAGAGGT GGGAGTGCTC GAAAGAGAAC CGGCGCACAG
GTGCTGCATG GCTGTCGTCA GCTCGTGTCG TGAGATGTTG GGTTAAGTCC CGCAACGAGC
GCAACCCTTG TCCTTAGTTG CTACGCAAGA GCACTCTAAG GAGACTGCCG GTGACAAACC
GGAGGAAGGT GGGGATGACG TCAAGTCCTC ATGGCCCTTA TGGGTAGGGC TCACACGTCA

TACAATGGTC GGAACAGAGG GTTGCCACCC GCGAAGGGGA GCTAATCCCA GAAAACCGAT
CGTAGTCCGG ATTGCACTCT GCACCTCGAG TGCATGAAGC TGGAATCGCT AGTAATCGCG
GATCAGCATG CCGCGGTGAA TACTTTCCCG GGTTTTGTAC ACACCGCCCG TCACACCATG
GGAGTGGGTT TTACCAGAAG TGGCTAGTCT AACCGCAAGG AAGAACGGTC CCCACGGTAG
GATTCATGAC TGGGTGAAGT CGTAACAAGT AGCCGTATCC GAAAGTTCGG CTGGA - 3'
```

FIG. 1

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 1495 base pairs
      (B) TYPE: nucleic acid
      (C) STRANDEDNESS: unknown
      (D) TOPOLOGY: unknown (ii) MOLECULE TYPE: Genomic DNA (xi) SEQUENCE DESCRIPTION: SEQ ID NO:1:

```
AAATATTACG CTGGTTGCAT GCCTTACAGC ATGCAAGTCG AACGGCAGCA CGGGTGCTTG      60

CACCTGGTGG CGAGTGGCGA ACGGGTGAGT AATACATCGG AACAATGTCC TGTAGTGGGG     120

GATAGCCCGG CGAAAGCCGG ATTAATACCG CATACGATCT ACGGATGAAA GCGGGGGACC     180

TTCGGGCCTC GCGCTATAGG GTTGGCCGAT GGCTGATTAG CTAGTTGGTG GGGTAAAGGC     240

CTACCAAGGC GACGATCAGT AGTTGTCTGA GAGGACGACC AGCCACACTG GGACTGAGAC     300

ACGGCCCAGA CTCTTACGGG AGGCAGCAGT GGGGAATTTT GGACAATGGG CGAAAGCCTG     360

ATCCAGCAAT GCCGCGTGTG TGAAGAAGGC CTTCGGGTTG TAAAGCACTT TTGTCCGGAA     420

AGAAATCCTT GGTTCTAATA TAGCCGGGGG ATGACGGTAC CGGAAGAATA AGCACCGGCT     480

AACTACGTGC CAGCAGCCGC GGTAATACGT AGGGTGCGAG CGTTAATCGG AATTACTGGG     540
```

```
CGTAAAGCGT GCGCAGGCGG TTTGCTAAGA CCGATGTGAA ATCCCCGGGC TCAACCTGGG      600

AACTGCATTG GTGACTGGCA GGCTAGAGTA TGGCAGAGGG GGGTAGAATT CCACGTGTAG      660

CAGTGAAATG CGTAGAGATG TGGAAGAATA CCGATGGCGA AGGCAGCCCC CTGGGCCAAT      720

ACTGACGCTC ATGCACGAAA GCGTGGGGAG CAAACAGGAT TAGATACCCT GGTAGTCCAC      780

GCCCTAAACG ATGTCAACTA GTTGTTGGGG ATTCATTTCC TTAGTAACGT AGCTAACGCG      840

TGAAGTTGAC CGCCTGGGGA GTACGGTCGC AAGATTAAAA CTCAAAGGAA TTGACGGGGA      900

CCCGCACAAG CGGTGGATGA TGTGGATTAA TTCGATGCAA CGCGAAAAAC CTTACCTACC      960

CTTGACATGG TCGGAATCCC GCTGAGAGGT GGGAGTGCTC GAAAGAGAAC CGGCGCACAG     1020

GTGCTGCATG GCTGTCGTCA GCTCGTGTCG TGAGATGTTG GGTTAAGTCC CGCAACGAGC     1080

GCAACCCTTG TCCTTAGTTG CTACGCAAGA GCACTCTAAG GAGACTGCCG GTGACAAACC     1140

GGAGGAAGGT GGGGATGACG TCAAGTCCTC ATGGCCCTTA TGGGTAGGGC TCACACGTCA     1200

TACAATGGTC GGAACAGAGG GTTGCCACCC GCGAAGGGGA GCTAATCCCA GAAAACCGAT     1260

CGTAGTCCGG ATTGCACTCT GCACCTCGAG TGCATGAAGC TGGAATCGCT AGTAATCGCG     1320

GATCAGCATG CCGCGGTGAA TACTTTCCCG GGTTTTGTAC ACACCGCCCG TCACACCATG     1380

GGAGTGGGTT TTACCAGAAG TGGCTAGTCT AACCGCAAGG AAGAACGGTC CCCACGGTAG     1440

GATTCATGAC TGGGTGAAGT CGTAACAAGT AGCCGTATCC GAAAGTTCGG CTGGA          1495
```

NON-OBLIGATE PREDATORY BACTERIUM *BURKHOLDERIA CASIDAE* AND USES THEREOF

This application is a continuation-in-part of provisional application Ser. No. 60/044,532, filed Apr. 23, 1997, the disclosure of which is incorporated herein by reference in its entirety.

1. FIELD OF THE INVENTION

The present invention relates to predator bacteria that have biocontrol activity against microorganisms. More particularly, the present invention is directed to a novel, non-obligate predator bacterium *Burkholderia casidae* (including variants thereof). The invention is also directed to methods for isolating and producing substantially pure cultures of *Burkholderia casidae*, and to antimicrobial preparations produced from such cultures. The invention is further directed to biocontrol compositions comprising such pure cultures, extracts and filtrates of such cultures, cell fractions prepared from such cultures, and antimicrobial preparations produced from *Burkholderia casidae*. The invention is additionally directed to methods for protecting plants against microbial diseases by treatment with biocontrol compositions of the invention.

2. BACKGROUND OF THE INVENTION

Past attempts to control plant microbial diseases have included the use of chemicals. However, many chemicals that have been in long-time use are now ineffective due to the increasing number of chemical-resistant strains of plant pathogens. Further, many such chemicals are recognized to be potentially hazardous to non-target organisms, particularly humans, and to the environment.

Biological control of plant pathogens, is an alternative to chemical control. It has been recognized that crops grown in some soils naturally are resistant to certain fungal pathogens. Furthermore, soils that are conducive to the development of fungal diseases can be rendered suppressive, or resistant, by the addition of small quantities of soil from a suppressive field. Scher et al., *Phytopathology* 70:421 (1980). Conversely, suppressive soils can be made conducive to fungal diseases by autoclaving or chemical fumigation, indicating that the factors responsible for disease control are biological. Root colonizing bacteria have been shown to be responsible for this phenomenon, which is known as biological disease control. Baker et al., *Biological control of plant pathogens,* Freeman Press, San Francisco (1974).

In many cases, the most efficient strains of biological disease controlling bacteria are fluorescent Pseudomonads. Weller et al., *Phytopathology*, 73: 463–469 (1983). Many biological control Pseudomonas strains produce metabolites, such as antibiotics and sideophores, that inhibit the growth of fungal pathogens. Howell et al., *Phytopathology* 69: 480–482 (1979); Howell et al., *Phytopathology* 70: 712–715 (1980).

An important factor in biological control is the ability of an organism to compete in a given environment. Thus, it is desirable to obtain novel biocontrol agents which effectively control (e.g., retard, restraint, kill, lyse) the growth of plant pathogens, particularly fungi, and which are able to aggressively compete with indigenous bacteria and other microflora that can exist on the surfaces or the rhizosphere of the plant.

3. SUMMARY OF THE INVENTION

The present invention generally relates to predator bacteria. More particularly, the invention is directed to a novel, non-obligate predator bacterium *Burkholderia casidae*, which has biocontrol activity against a broad range of microorganisms, particularly microbial pathogens. One aspect of the invention is directed to substantially pure cultures of *B. casidae* (including variants), and to methods for isolating and producing such substantially pure cultures. In a preferred embodiment, the invention provides a substantially pure culture of *B. casidae* strain 2.2N (ATCC accession no. 55961).

Another aspect of the invention is directed to preparations of antimicrobial compounds produced by *B. casidae,* and to methods for producing such antimicrobial preparations. In a preferred embodiment, the invention provides antimicrobial preparations comprising antifungal and anti-yeast compounds produced by *B. casidae* strain 2.2N or variants thereof, and methods for producing such preparations.

An additional aspect of the invention is directed to biocontrol compositions comprising materials obtained or derived from *B. casidae*, cells or cultures, and to methods for producing such biocontrol compositions. In one embodiment, the biocontrol compositions comprise live *B. casidae* cells or cultures. In another embodiment, the biocontrol compositions comprise inactivated *B. casidae* cells or cultures that may have been processed in a variety of ways including cell breakage and spray drying. In an additional embodiment, the biocontrol compositions comprise cell-free filtrates or cell fractions prepared from *B. casidae* cells or cultures. In a further embodiment, the biocontrol compositions comprise preparations of antimicrobial compounds isolated from *B. casidae*, cells or cultures, or cell-free filtrates or cell fractions prepared from such cultures or cells. In preferred embodiments, the biocontrol compositions comprise cells (living or dead) or cultures (living or dead) of *B. casidae* strain 2.2N, or cell-free filtrates or cell fractions, or antimicrobial, particularly anti-fungal, preparations made from such cells or cultures.

A further aspect of the invention is directed to methods for the prevention and/or treatment of plant microbial diseases using biocontrol compositions of the invention. In one embodiment, the methods for prevention and/or treatment comprise treating the plants themselves with an effective amount of a biocontrol composition. In another embodiment, the methods for prevention and/or treatment comprise treating plant seeds prior to planting with an effective amount of a biocontrol composition. In a further embodiment, the methods for prevention and/or treatment comprise treating the soil in the immediate vicinity of the plant with an effective amount of a biocontrol composition. In preferred embodiments, the methods of the invention are directed to prevention and/or treatment of plant fungal diseases using biocontrol compositions of the invention.

*B. casidae* (including variants thereof) of the invention exerts biocontrol activity against a wide spectrum of microorganisms. *B. casidae* adversely affects the growth or survival of such microorganisms in its vicinity. Because some of the antimicrobial activity of *B. casidae* is present in cell-free culture-filtrates, biocontrol activity is soluble in water and can exert its activity against microorganisms in aqueous suspension. Antimicrobial activity does not require living cells or cell contact. Susceptible microorganisms are referred to herein as prey or targets of *B. casidae*. Prey of *B. casidae* include, but are not limited to, fungi (including yeast), algae, protozoa, and bacteria (including blue green algae) other than *B. casidae*.

*B. casidae* exerts biocontrol activity against a particular prey microorganism in its vicinity by releasing one or more antimicrobial compounds that adversely affect the growth or survival of the prey, and/or by physically attacking the prey through attachment, subsequent parasitism and eventual destruction of the prey. Different prey microorganisms are susceptible to different combinations of such actions by *B. casidae*. Some prey are susceptible only to physical attack by *B. casidae*. Other prey are susceptible only to a particular one, or combination, of the antimicrobial compounds released by *B. casidae*. Yet other prey are susceptible to both physical attack and one or more of the released antimicrobial compounds.

Since many prey microorganisms of *B. casidae* are pathogens, the antimicrobial preparations and biocontrol compositions of the invention beneficially may be used in the prevention and/or treatment of microbial diseases of plants and animals including humans. In particular, the antimicrobial preparations of the invention may be used to manufacture medicaments for use in treatment of microbial diseases of animals, fish, and humans, and to produce bactericides and fungicides for use in controlling microbial diseases, particularly those of plants. The biocontrol compositions of the invention may be directly used to prevent and/or treat microbial, particularly fungal, diseases of plants. The antimicrobial compounds and biocontrol compositions of the invention also may be used to treat, or prevent, protozoan diseases, and to control protozoan and algal growth in aquatic environments.

The present invention may be understood more fully by reference to the following detailed description of the invention, examples of specific embodiments of the invention and the appended figure.

3.1. DEFINITIONS

In order to provide a clear and consistent understanding of the specification and claims, including the scope to be given to a term, the following definitions are given to various terms and abbreviations used herein.

| | |
|---|---|
| 2.2N | *Burkholderia casidae* strain 2.2N (ATCC accession no. 55961); also referred to as "strain 2.2N". |
| antifungal | as used herein, the term "antifungal" includes anti-yeast activity, unless indicated otherwise. |
| antimicrobial compound | A compound that has one or more adverse effects against a microorganism, such as retarding, suppressing or stopping growth of the microorganism or killing or lysing the microorganism. The adverse effect on growth may be temporary or permanent. An antimicrobial compound may be more particularly an anti-filamentous fungi compound, anti-mycobacteria compound, anti-yeast compound, anti-algal compound, anti-protozoan compound and/or antibacterial compound. |
| B. casidae | *Burkholderia casidae*. As used herein, the term "B. casidae", unless otherwise modified, encompasses the B. casidae species and all B. casidae strains and variants thereof. |
| B. casidae variant | A B. casidae variant is a mutant or derivative of a B. casidae strain. The mutation in a mutant may be chromosomal or extrachromosomal, and may be spontaneous or artificially-induced. Derivatives include B. casidae strains and mutants that contain deletion or insertion of DNA. Also included are B. casidae strains and mutants that have lost a bacteriophage (i.e., as prophage) or plasmid, or one or more segments of a chromosomal, plasmid, or bacteriophage (i.e., as prophage) DNA that may be found in B. casidae. Derivatives can also include B. casidae strains and mutants that contain one or more extrachromosomal genetic elements, such as an insertion sequence or transposon or a plasmid or bacteriophage. |

-continued

| | |
|---|---|
| BHIM | Brain Heart Infusion Medium, one-tenth strength Brain Heart Infusion Broth (Difco, Detroit, MI). |
| BHIM agar | BHIM with 1.5% agar. |
| biocontrol | The ability to retard or suppress the growth of a microorganism, or to kill or lyse the microorganism. |
| cell fractions | Cells can be broken to obtain, for example, the following cell fractions: cell walls, cell membranes, soluble material, and particulate material. |
| cell-free filtrate | Medium of culture from which cells have been removed by, for example, filtration, centrifugation or precipitation. |
| cells | Cells recovered from culture. |
| culture | Cells with medium in which cells have been grown. |
| culture fractions | Cells and cell-free culture medium recovered from cultures. |
| cysts | Resting stage of cells with a thicker cell wall. |
| filter-sterile | A term used to describe a process applied to a solution, culture medium, etc. that removes any microorganisins therefrom by passing such liquid materials through a porous membrane or matrix and hence separates the cells from the liquid. |
| fungi | The term includes filamentous fungi and yeast. |
| GSM | Glutamate Synthetic Medium, 0.1% L-glutamic acid, 0.05% $MgCl_2.6H_2O$, 0.1% $KH_2PO_4$, 0.1% $NH_4NO_3$, 0.02% $Na_2SO_4$, and 0.02% NaCl (pH 7.0). |
| HIB | Heart Infusion Broth (Difco, Detroit, MI) |
| microorganism | A bacterium, fungus (including yeast), alga, or protozoan whose cells can be best viewed by magnification (i.e., a microscope). |
| nitrogen-limiting | The condition where the nitrogen nutrient of the medium is, or would be, exhausted before the exhaustion of any other essential nutrients, such as carbon. |
| pasteurized | Process of heating (i.e., 80° C. for approximately 15 min) to kill cells; process can be applied to any culture or cell fraction. |
| PCR | Polymerase chain reaction. |
| prey | A prey microorganism. A microorganism whose growth or survival is adversely affected by a predator bacterium, such as B. casidae, present in its immediate vicinity. The adverse effect may be due to physical attack (contact) or release of one or more antimicrobial compounds by the predator bacterium. Also known as target organism. |
| rRNA | Ribosomal RNA. |
| soil eluate | The water or media wash of a soil sample. Also referred to as "percolation" fluid. |
| spp. | Plural of species. |
| substantially pure culture | A culture of subject microorganism that is substantially free of any contaminant microorganisms (i.e., other types or species of microorganisms). Specifically, a substantially pure culture is at least 75% (i.e., containing less than one contaminant microorganism |

| | |
|---|---|
| | per three subject microorganism), preferably at least 90%, more preferably at least 99.9%, and most preferably 100%, free of any contaminant microorganisms. |
| TSM | One-quarter strength Tryptic Soy Broth (Difco, Detroit, MI). |
| TSM + S | TSM with 0.2% (w/v) sucrose. |
| yeast | The term does not include filamentous fungi. |

4. BRIEF DESCRIPTION OF THE FIGURE

FIG. 1 depicts the partial nucleotide sequence (from positions 27 to 1522; approximately 98%) of 16S rRNA (SEQ ID NO:1) of *Burkholderia casidae* strain 2.2N, which was PCR amplified from genomic DNA using primers 27f (SEQ ID NO:2) and 1522r (SEQ ID NO:3).

5. DETAILED DESCRIPTION OF THE INVENTION

The present invention relates to a novel, non-obligate predator bacterium, *Burkholderia casidae*, that has biocontrol activity against a wide spectrum of microorganisms. The invention provides substantially pure cultures of *B. casidae* (including variants thereof), as well as methods for producing and recovering such cultures. The invention also provides purified antimicrobial compounds produced by *B. casidae*. The invention further provides biocontrol compositions comprising *B. casidae* cells or cultures, cell-free filtrates or cell fractions of such cells or cultures; or antimicrobial preparations made from such cultures cells, or cell fractions; and methods for producing said biocontrol compositions. The invention further provides methods for preventing or treating plant microbial diseases by the application of biocontrol compositions of the invention.

A specific embodiment of the invention, *B. casidae* strain 2.2N, has at least four distinct antimicrobial activities: (1) antibacterial, (2) anti-mycobacterial, (3) anti-filamentous fungi, and (4) anti-yeast. The distinction between the anti-filamentous fungi activity and the anti-yeast activity is based on differences in the heat-stability of each activity in cell-free materials, such as filtrates, obtained from strain 2.2N cultures (i.e., the anti-yeast activity is relatively more heat-resistant). In addition, strain 2.2N produces one or more proteases that have broad spectrum antimicrobial activities. Strain 2.2N also has anti-algal and anti-protozoan activities.

5.1. *Burkholderia casidae* Strains

*B. casidae* is a naturally occurring, gram-negative soil bacterium. Its existence and isolation had not been previously described. When cultivated in artificial media, *B. casidae* can exist in at least two alternate structural forms. *B. casidae* exists in the so called cell form when it is grown in artificial media that are not limited for nitrogen nutrients. The cell form of *B. casidae* is a short, motile rod approximately 1 μm in length and approximately 0.5 μm in diameter. *B. casidae* also can exist in the so-called cyst form when cultivated in artificial medium. The cyst form of *B. casidae* is a spherical structure approximately 1.25 μm in diameter and comprises a central body approximately 0.25 μm in diameter and a coat that surrounds the central body. *B. casidae* cells differentiate into cysts when nitrogen nutrients in the media become growth limiting. The cyst form of *B. casidae* is not more heat or desiccation resistant than the cell form. Heat or chemical treatment of *B. casidae* cysts significantly increases the release rate of antimicrobial, particularly anti-fungal, compounds from the cysts.

*B. casidae* exhibits biocontrol activity against a wide spectrum of prey microorganisms. As discussed above, the biocontrol activity of *B. casidae* against a particular prey microorganism may be due to physical attack on the prey and/or the release of one or more antimicrobial compounds that adversely affect the prey. *B. casidae* cell produces a range of antimicrobial compounds that are (1) stored intracellularly, (2) associated with cells, cysts, or cell and cyst fractions (e.g., cell walls), or (3) are found in the medium outside of, and not associated with, cells due to either active export, secretion, or cellular lysis.

Fungi that are prey of *B. casidae* include saprophytes as well as pathogens of plants, animals and humans. Prey fungi include, but are not limited to, those in any of the following genera: Agaricus, Alternaria, Aspergillus, Botrytis, Candida, Cercospora, Cercosporidium, Cryptococcus, Geotrichum, Mycosphaerella, Mucor, Penicillium, Phoma, Phytophthora, Plasmopora, Pseudopeziza, Puccinia, Pythium, Rhizoctonia, Rhizopus, Saccharomyces, Septoria, Sporothrix, Stemphylium, Trichophyton, and Verticillium. Bacterial prey of *B. casidae* include, but are not limited to, those in any of the following genera: Agromyces, Arthrobacter, Micrococcus, Mycobacterium, Nocardia, Staphylococcus, and Streptomyces. Algal prey of *B. casidae* can be eukaryotic or prokaryotic and include, but are not limited to, those of the Anabena spp. Protozoan prey of *B. casidae* include, but are not limited to, those of the Paramecium and Tetrahymena spp.

A preferred embodiment of the invention is *B. casidae* strain 2.2N. In addition to having the above described biological and biocontrol characteristics, strain 2.2N also has the following particular genetic, biochemical, cultural, enzymatic, and metabolic characteristics.

Strain 2.2N has a 16S rRNA gene sequence comprising that of SEQ ID NO:1. As displayed in Table 3, infra, pairwise comparisons of 16S rRNA gene sequences show that strain 2.2N shares high sequence similarity with members of the genus Burkholderia (i.e., >85%). By contrast, *Escherichia coli* gave a similarity value of 71.7% (Table 3). The 16S rRNA data indicate strain 2.2N belongs to the Burkholderia genus.

Organisms sharing more than 97% rRNA similarity belong to a single species (Vandamme et al., 1996, Microbiol. Reviews 60:407–438). The 16S rRNA of strain 2.2N shares less than 95% sequence similarity with the 16S rRNA of known Burkholderia spp. Thus, strain 2.2N represents a novel Burkholderia species.

*B. casidae* strain 2.2N has a cellular fatty acid composition that differs markedly from those of other of Burkholderia species. Specifically, strain 2.2N has significantly less C16:0 fatty acids, almost no 16:1 fatty acids, almost no C17:CPA (cyclopropanylated) fatty acids, and high levels of both C18:1 (9,10 and 11,12) fatty acids and 2-OH C15:0 fatty acids (see Table 4, infra). This pattern appears to be unique among known Burkholderia spp., further supporting the conclusion that strain 2.2N represents a novel Burkholderia spp.

As assayed with the API50 CH test (bioMerieux Vitele, Inc., Hazelwood, Mo.), strain 2.2N can utilize all of the following compounds as substrates: adipate, caprate, D-fucose, galactose, glucose, mannitol, mannose, phenylacetate and sucrose as substrate; and cannot utilize any of the following compounds as substrate: 2-ketogluconate, cellobiose, D-arabinose, D-xylose, glycerol, inositol, L-arabinose, malate, rhamnose, sorbitol, and trehalose.

As assayed with the API-NFT test (bioMerieux S.A., Marcy-l'Etiole, France), strain 2.2N can grow at about 41°

C., reduce nitrate to nitrite, hydrolyze esculin and gelatin, and form indole. Strain 2.2N cannot produce yellow pigments, urease, arginine dihydrolase and cytochrome oxidase.

As assayed with the Sceptor Pseudomonas/Resistant MIC Panel (Becton-Dickinson, Sparks, Nev.), strain 2.2N is resistant to the antibiotics amikacin, cefoperazone, gentamycin, tetracycline, ticarcillin/clavulanic acid and tobramycin; and is susceptible to the antibiotics cefotaxime, ceftizoxime, ceftazidime, ceftriaxone, ciprofloxacin, imipenem, and trimethoprim/sulfamethoxazole.

A pure culture of *B. casidae* strain 2.2N was deposited on Apr. 23, 1997 with the American Type Culture Collection (ATCC), now located at 10801 University Boulevard, Manassas, Va. 20110-2209, in compliance with the provisions of the Budapest Treaty on the International Recognition of the Deposit of Microorganisms for the Purpose of Patent Procedure, and has been assigned ATCC accession number 55961.

The present invention contemplates all *B. casidae* strains and variants thereof. According to the invention, a *B casidae* strain has biocontrol, genetic, biochemical and metabolic characteristics that are substantially similar to those of strain 2.2N. Specifically, a *B. casidae* strain has a 16S rRNA gene comprising a sequence that is at least 97%, preferably at least 99%, and most preferably 100%, identical to the 16S rRNA gene sequence of strain 2.2N, which comprises the sequence of SEQ ID NO:1, as determined by Clustal Analysis.

A *B. casidae* strain also has cellular fatty acid content that is substantially similar to that of strain 2.2N, as shown in Table 4, infra. Specifically, a *B. casidae* strain has a fatty acid composition wherein (a) C16:0 fatty acid comprises from about 16% to about 20%, preferably about 18%, of the total cellular fatty acid content; (b) C16:1 fatty acid comprises from about 18% to about 22%, preferably about 21%, of the total cellular fatty acid content; and (c) C18:1 (11,12) fatty acid comprises from about 35% to about 45%, preferably about 39%, of the total cellular fatty acid content.

As assayed with the API50 CH test (bioMerieux S.A., Marcy-l'Etiole, France), a *B. casidae* strain can utilize at least seven, preferably at least eight, and most preferably nine, of the following compounds as substrate: adipate, caprate, D-fucose, galactose, glucose, mannitol, mannose, phenylacetate and sucrose; and can utilize no more than two, preferably no more than one, and most preferably none, of the following compounds as substrate: 2-ketogluconate, cellobiose, D-arabinose, D-xylose, glycerol, inositol, L-arabinose, malate, rhamnose, sorbitol, and trehalose.

5.1.1. Antimicrobial Compounds Produced by *Burkholderia casidae*

*B. casidae* produces and releases one or more antimicrobial compounds. Such compounds may achieve their adverse effects on a prey microorganism by acting alone or in combination with other antimicrobial compounds produced by *B. casidae.*

*B. casidae* produces one or more antimicrobial compounds that each alone or in combination have predominately anti-bacterial activity. Such antibacterial compounds are active against bacteria that include, but are not limited to, those from any of the Agromyces, Arthrobacter, Micrococcus, Mycobacterium, Nocardia, Staphylococcus, and Streptomyces genera. The antibacterial compounds produced by *B. casidae* are relatively heat-labile. For example, incubation of crude preparations of such compounds at about 80° C. for approximately 10 minutes causes approximately 100% loss of antibacterial activity.

*B. casidae* also produces one or more antimicrobial compounds that each alone or in combination have predominately anti-filamentous fungi activity. Such anti-filamentous fungi compounds collectively are active against filamentous fungi that include, but are not limited to, those from any of the following genera: Agaricus, Alternaria, Aspergillus, Botrytis, Cercospora, Cercosporidium, Cryptococcus, Geotrichum, Mucor, Penicillium, Phoma, Phytophthora, Plasmopora, Pseudopeziza, Puccinia, Pythium, Rhizoctonia, Rhizopus, Septoria, Sporothrix, Stemphylium, Trichophyton, and Verticillium. The anti-filamentous fungi compounds collectively also are active against Mycobacterium spp. and Anabena spp. In comparison to the antibacterial compounds produced by *B. casidae* cells, the anti-filamentous fungi compounds are relatively heat-stable. For example, crude preparations of anti-filamentous fungi compounds produced by *B. casidae* can withstand incubation at approximately 80° C. for about 10 minutes and suffer less than 35% loss of anti-filamentous fungi activity.

*B. casidae* also produces one or more antimicrobial compounds that each alone or in combination have predominantly anti-yeast activity. Such anti-yeast compounds are active against yeast that include, but are not limited to, those from any of the following genera: Candida, Cryptococcus, and Saccharomyces. In comparison to the antibacterial and the anti-filamentous fungi compounds produced by *B. casidae*, the anti-yeast compounds produced are very heat-resistant. For example, crude preparations of anti-yeast compounds produced by *B. casidae* can withstand incubation at approximately 80° C. to 100° C. for about 10 minutes and incur less than 5% loss of anti-yeast activity.

*B. casidae* cysts produce and accumulate anti-filamentous fungi and anti-yeast compounds. The cysts release such compounds at a relatively slow rate. The release rate can be increased significantly by inducing the cysts to grow, particularly by incubating the cysts in fresh, nitrogen-rich media at about 28° C. The rate of release also can be increased by exposing the cysts to boiling or autoclaving, and/or by treating the cysts with various organic solvents, such as alcohols.

Except under special conditions (see below), *B. casidae* cultures may comprise mixtures of cells and cysts. Further, the relative amounts of cells and cysts in such cultures may change in response to changing culture conditions (e.g., the relative levels of carbon and nitrogen nutrients). Accordingly, most *B. casidae* cultures, through their life-cycle, typically produce all the antibacterial, anti-yeast and anti-filamentous fungi compounds that are associated with cells or found in the medium.

5.2. Cultures of *Burkholderia casidae* and Variants 5.2.1. Isolation and Purification of *B. casidae*

The present invention provides substantially pure cultures of *B. casidae* (including variants thereof). Such substantially pure cultures may be obtained by a method comprising: isolating non-obligate predator bacteria, which include *B. casidae*, from soil; purifying the predator bacteria isolates; screening and identifying the isolates for those that have the unique genetic and biochemical characteristics of *B. casidae*; and growing the *B. casidae* isolates, thereby producing substantially pure cultures of *B. casidae.*

The isolation, identification, and production of substantially pure cultures of *B. casidae* are carried out using standard microbiological techniques. Examples of such techniques may be found in Gerhardt, P. (ed.) *Methods for General and Molecular Microbiology.* American Society for Microbiology, Washington, D.C. (1994) and Lennette, E. H. (ed.) *Manual of Clinical Microbiology,* Third Edition. American Society for Microbiology, Washington, D.C. (1980).

Non-obligate, predator bacteria can be isolated from many different types of soil. Preferably the soil is from the temperate or subarctic region in North America. Useful soils include various types of loam soil, such as silty clay loam, silt loam, clay loam and loam. A preferred source for isolating of *B. casidae* is loam type soil from fallow agricultural fields The isolation of *B. casidae* from soil optionally can be preceded by treatment of the source material with one or more mutually, non-exclusive enrichment procedures that increase the absolute number or relative amount of *B. casidae* in the sample material. The source material may be subjected to a single enrichment procedure or several different enrichment procedures in sequence, prior to use in isolating *B. casidae*.

In one enrichment procedure, a soil sample or soil eluate (i.e., an aliquot of a water or media wash of the soil sample) is incubated with an inoculum of a prey microorganism of *B. casidae* for several days, at about 28° C., under conditions conducive to the growth of *B. casidae* (see below for such conditions). The prey microorganism serves as a food source for *B. casidae* and thereby increases the level of *B. casidae* in the source material. In one embodiment, the prey microorganism used in the enrichment procedure is *Micrococcus luteus*. In another embodiment, the prey microorganism is *Saccharomyces cerevisiae*.

In another enrichment procedure, a soil sample or soil eluate is plated on a copper-containing agar medium and incubated at about 28° C. for several days to select for copper-resistant bacteria, which include *B. casidae*. Colonies that grow on a copper-containing medium are candidates for predator testing and/or screening for *B. casidae*. In one embodiment of this procedure, the selection agar medium contains 0.25% (w/v) Brain Heart Infusion Broth (Difco), 0.01% (w/v) $CuCl_2.2H_2O$ and 1.5% (w/v) agar pH 6.5.

In yet another enrichment procedure, a soil sample or soil eluate is plated on Noble agar containing a small amount (e.g., about 1% [v/v]) of *Arthrobacter globiformis* culture filtrate and incubated at 28° C. for several days to select for bacteria that can grow on such a medium. Colonies that have a "fried-egg" or "beehive" appearance on this medium are candidates for predator testing and/or screening for *B. casidae*.

In yet a different enrichment procedure, a soil sample or soil eluate is plated on minimal medium that lacks a carbon source and contains only a minimal level of nitrogen nutrients and incubated for several days to select for bacteria that can grow on such medium. Colonies that have a "fried-egg" or "beehive" appearance are preferred candidates for subsequent predator testing and/or screening for *B. casidae*. In an embodiment, the enrichment procedure uses a modified Burk Azotobacter medium comprising 0.08% $K_2HPO_4$, 0.02% $KH_2PO_4$, 0.02% $MgSO_4.7H_2O$, 0.01% $CaSO_4.2H_2O$ 0.25 mg/L $NaMoO_4.2H_2O$, 8.6 mg/L $Fe(NH_4)_2(SO_4)_2.12H_2O$, and 1.5% Noble agar.

*B. casidae* may be isolated by first isolating predator bacteria from a source material. The source material may be a untreated soil or soil eluate, or a enriched product of such sample materials prepared as described above. Predator bacteria can be isolated by plating a small amount of the source material on an agar medium previously inoculated with a sparse lawn of a prey microorganism of *B. casidae*, and examining for colonies that are surrounded by a zone of clearing or inhibition of the prey microorganism after several days of incubation at about 28° C. The sparse lawn of prey microorganism may be prepared in the form of a top-agar overlay or a spread of a bacterial inoculum on a base agar medium that can support growth of the prey. In one embodiment, the prey microorganism is *M. luteus* and the base agar medium is BHIB agar (0.25% (w/v) Brain Heart Infusion Broth, 1.5% (w/v) agar). In another embodiment, the prey microorganism is *Staphylococcus aureus* and the base agar medium is BHIM agar. In yet another embodiment, the prey organism is *S. cerevisiae* and the base agar medium is BHIM agar.

Bacterial colonies that produce a zone of clearing or inhibition of prey microorganism are tested for predator activity by streaking a sample of the colony perpendicularly across a streak of a prey microorganism on a plate of agar medium that can support the growth of the prey, and incubating the test plate at about 28° C. for several days. Predator bacteria are those whose growth spreads and tracks along with the track of the prey microorganism and lyses the prey microorganism at the intersections of the bacterial streaks. In one embodiment, the predator test uses *M. luteus* as the prey microorganism. In another embodiment, the test uses *S. cerevisiae* as the prey organism.

A predator bacteria isolate may be purified from any contaminant microorganism using any technique known in the art. For example, a predator bacteria isolate may be purified by several rounds, preferably at least three rounds, of streaking or plating the isolate from a single, isolated colony. Agar media that may be used for the isolation, purification and maintenance of *B. casidae* strains include, but are not limited to, HIB agar, BHIM agar, TSM agar (TSM with 1.5% agar) and their equivalents.

To isolate *B. casidae*, the purified predator bacteria isolates are screened for those that have the biological, genetic, biochemical and/or enzymatic characteristics of *B. casidae*. According to the invention, a predator bacteria is *B. casidae* if it has the 16S rRNA gene sequence and the cellular fatty acid profile of *B. casidae* as described in Section 5.1, above.

5.2.1.1. *B. casidae* Variants

The invention also provides variants of *B. casidae*, which comprise naturally-occurring and artificially-constructed mutants and derivatives of *B. casidae*. The *B. casidae* variants have substantially the same 16S rRNA gene sequence (i.e., ≧95% identity) and cellular fatty acid profile as those described in Section 5.1, above, for *B. casidae*. Variants may have a different number of rRNA cistrons as well. *B. casidae* variants of the invention may vary in their biocontrol activity and/or production of antimicrobial compounds as compared to, for example, wild-type strain 2.2N. Variants also may have different colonial morphology, colonial pigmentation, and growth rate characteristics. Variants may also have a different spectrum of antimicrobial activities and enzymatic activities. Preferred *B. casidae* variants of the invention are those that have biocontrol activity identical or superior to that of the corresponding wild-type *B. casidae* strain (e.g., strain 2.2N). As used herein, superior biocontrol activity means an adverse effect on a wide spectrum of prey microorganisms, and/or production of a higher level and/or greater number of antimicrobial compounds.

Naturally-occurring *B. casidae* variants may be isolated from soil, purified and identified using approaches and methods described in section 5.2.1. above. Spontaneous *B. casidae* variants may be isolated by screening a *B. casidae* strain on agar media for variants in colony morphology and/or inhibitory activity against a prey microorganism. In an embodiment, *B. casidae* variants may be isolated by screening strain 2.2N.

*B. casidae* variants also may be artificially constructed from *B. casidae* strains (e.g., strain 2.2N) using methods known in the art of bacterial genetics and recombinant DNA technology. For example, *B. casidae* mutants may be produced by mutagenizing *B. casidae* strains with chemical mutagens or irradiation, and selecting or screening for isolates that have the desired alterations in phenotype and/or genotype (e.g., biocontrol activity against one or more prey microorganism). *B. casidae* derivatives may be produced from *B. casidae* strains by bacterial conjugation; transformation with DNA, including plasmid and phage DNA; or transduction or transfection with phages. *B. casidae* derivatives may also be produced as a consequence of the introduction of insertion sequences (IS) or transposons (Tn) via conjugation, transformation, or transduction. The following references provide exemplary teachings of genetic and/or recombinant DNA techniques that may be used to construct such *B. casidae* variants: Gerhardt, P. (ed.) *Methods for General and Molecular Microbiology.* American Society for Microbiology, Washington, D.C. (1994); Berger and Kimmel, *Guide to Molecular Cloning Techniques,* Methods in Enzymology, Volume 152. Academic Press, NY, (1987); Cheng and Lessie, 1994, "Multiple replicons constituting the genome of *Pseudomonas cepacia,*" J. Bacteriol. 176:4034–4042; Simon et al., "A broad host range mobilization system for in vivo genetic engineering: transposon mutagenesis in Gram-negative bacteria," Bio/Technology, November 1983, pages 784–791; Darzins and Chakrabarty, 1984, "Cloning of genes controlling alginate biosynthesis from a mucoid cystic fibrosis isolate of *Pseudomonas aeruginosa,*" J. Bacteriol. 159:9–18; Irani and Rowe, 1997, "Enhancement of transformation in *Pseudomonas aeruginosa* PAO1 by $Mg^{2+}$ and heat," BioTechniques 22:45–56; Lennon and DeCicco, 1991, "Plasmids of *Pseudomonas cepacia* strains of diverse origin," Applied Environ. Microbiol. 57:2345–2350; and U.S. Pat. No. 5,639,949.

5.2.2. Growth of *B. casidae*

*B. casidae* may be grown aerobically at about 20° C. to about 41° C., preferably at about 28° C. to about 30° C., on any solid or liquid medium that will support its growth. Useful media for growing *B. casidae* include, but are not limited to, BHIM, TSM+S, and MSB medium composed of 1% molasses (or 1% corn syrup) and 1% soy bean meal (or 1% peanut meal or 1% cotton seed meal). MSB medium and equivalents are particularly useful for production of large volume cultures because of their low cost. Synthetic media such as GSM may also be used to grow *B. casidae.*

The invention provides cultures of *B. casidae* cells (in contrast to *B. casidae* cysts). According to the invention, cultures of *B. casidae* cells contain at least 80%, preferably at least 95%, and most preferably at least 99%, cells. Cultures of *B. casidae* cells can be prepared by growing *B. casidae* in media that are not nitrogen-limiting, and harvesting the cultures at any time from early log phase to stationary phase. Media that have balanced carbon and nitrogen nutrients are not nitrogen-limiting. Such media are especially useful for producing cultures of *B. casidae* cells. Examples of balanced carbon and nitrogen nutrient media include GSM and media composed essentially of prey microorganisms of *B. casidae.*

Cultures of *B. casidae* cells also can be prepared by growing *B. casidae* in any medium that will support their growth, and harvesting the cultures before nitrogen nutrients become limiting. Media that can be used in this manner to produce cultures of cells include BHIM, TSM and MSB. The optimal time for harvesting cultures of *B. casidae* cells grown in such media can be determined by monitoring the culture's cell and cyst content by microscopy. Typically, log phase is the optimal time for harvesting cultures of *B. casidae* cells grown in such media.

The invention also provides cultures of *B. casidae* cysts. According to the invention, cultures of *B. casidae* cysts contain at least 80%, preferably at least 95%, and most preferably at least 99% percent cysts.

Cultures of *B. casidae* cysts can be prepared by growing *B. casidae* in media that are nitrogen-limited and harvesting the cultures after nitrogen nutrients become limiting or have been exhausted. Media that can be used for producing cultures of cysts include TSM+S. The optimal time for harvesting cultures of *B. casidae* cysts grown in such media can be determined by monitoring cultures' cell and cyst content. Typically, stationary phase is the optimal time for harvesting cultures of cysts produced in such media.

Cultures of *B. casidae* cysts also can be prepared by growing or incubating at 28° C., *B. casidae* cells in media that are nitrogen-deficient and harvesting the cultures after any residual media and intracellular nitrogen nutrients have been exhausted. Media that can be used for producing cultures of cysts in this manner include Burk's Broth (0.064% [w/v] $K_2HPO_4$, 0.016% [w/v] $KH_2PO_4$, 0.005% [w/v] $CaSO_4 \cdot 2H_2O$, 0.02% [w/v] $MgSO_4 \cdot 7H_2O$, 0.02% [w/v] NaCl, 1.0% [w/v] sucrose). The optimal time for harvesting cultures of cysts from such media can be determined by monitoring the cultures for their cyst content by microscopy. Typically, the optimal time for harvesting cultures of cysts produced in such media is after growth has ceased and the cultures are in the stationary phase of growth.

Cultures of *B. casidae* grown and harvested under conditions other than those described above may contain vegetative cells and/or cysts. The vegetative cell and cyst contents of the cultures can be determined by microscopy.

5.3. Antimicrobial Preparations

The invention provides antimicrobial preparations containing antifungal (including anti-filamentous fungi and anti-yeast) compounds produced by *B. casidae.* The antimicrobial preparations of the invention comprise alcohol-extracts of *B. casidae* cells, cysts, culture, suspension, cell-free filtrate or cell fraction, which alcohol-extracts can be prepared by extracting any of the foregoing materials with an alcohol and concentrating the alcohol soluble material.

In an embodiment, the antimicrobial preparation can be produced by a method comprising boiling an alcoholic mixture comprising the cell, culture, suspension, cell-free filtrate or cell fraction and an alcohol; clarifying the boiled mixture; mixing the boiled mixture with magnesium silicate (talc); collecting the magnesium silicate; washing the magnesium silicate with water; and eluting antifungal compounds from the magnesium silicate with an alcoholic solution. One skilled in the art can determine the optimal conditions for each of these steps, and indeed the entire procedure, by varying each step in a systematic fashion and assaying for the antimicrobial activity recovered under each variation using routine assay procedures.

In a preferred embodiment, a method for producing the antimicrobial preparation of the invention comprises the following: Isopropanol is added to a *B. casidae* culture, or its cell-free filtrate or cell fraction, or a suspension of *B. casidae* cells and/or cysts to a final concentration of about 47% (v/v). The solution is boiled for a short period and then cooled. The extraction solution is clarified by centrifugation and concentrated three-fold by vacuum evaporation at 65° C. Magnesium silicate is added to the concentrated extraction solution to approximately 8% (w/v) and the suspension stirred for about 30 min at room temperature. The magnesium silicate is collected and washed with water. Absorbed materials, including antifungal compounds, are eluted from the washed magnesium silicate with 70% isopropanol solution and dried by vacuum evaporation at 65° C. and thereby yielding the antimicrobial preparation.

The antimicrobial preparations of invention are soluble in water or alcohol and have biocontrol activity against substantially the same spectrum of filamentous fungi and yeast as that described above for *B. casidae* culture.

5.4. Biocontrol Compositions

The invention also provides biocontrol compositions that can be used to treat or prevent various microbial diseases of plants, animals and humans, and to control the growth of algae and protozoa in aquatic environments. Biocontrol compositions of the invention comprise *B. casidae* cells, cysts or cultures; cell-free filtrates or cell fractions of *B. casidae* cultures, cells or cysts; spray- or freeze-dried cultures or cell pastes (i.e., isolated cells); or antimicrobial preparations produced from *B. casidae* cultures, cells, cysts, cell-free filtrates or cell fractions.

The biocontrol compositions of the invention contain essentially one or several of three different types of active ingredients. One type of active ingredient is the bacterium *B. casidae* itself, which can exert biocontrol activity by physically attacking a prey microorganism and/or by the presence of extracellular antimicrobial compounds that are antagonistic to the prey microorganism. A second type of active ingredient is inactivated *B. casidae* cells or cysts, which exert biocontrol activity through the release of intracellularly stored antimicrobial compounds. A third type of active ingredient is the antimicrobial compounds present in the medium of *B. casidae* culture or released from cells. A culture or suspension of live *B. casidae* contains the first and third types of active ingredients. A culture or suspension of inactivated *B. casidae* contains the second and third types of active ingredients. A cell-free filtrate or cell fraction of *B. casidae* culture, or cell or cyst suspension, contains the third type of active ingredient.

5.4.1. Liquid Biocontrol Compositions

The biocontrol compositions of the invention may be in form of a liquid or solid.

Liquid biocontrol compositions of the invention comprise liquid cultures of *B. casidae*; suspensions of *B. casidae* cells and/or cysts; cell-free filtrates or cell fractions of *B. casidae* cultures or suspensions; suspensions of spray- or freeze-dried *B. casidae* cultures or cells; and/or antimicrobial preparations.

In one embodiment, liquid biocontrol compositions comprise liquid cultures or suspensions of live *B. casidae*. Preferably, such biocontrol compositions comprise cultures or suspensions of *B. casidae* strain 2.2N. More preferably, such biocontrol compositions comprise stationary cultures of strain 2.2N grown in a nitrogen-limited medium, such as TSM+S, or suspensions of strain 2.2N harvested from such cultures.

In another embodiment, liquid biocontrol compositions comprise inactivated (i.e., sterilized) cultures or suspensions of inactivated *B. casidae*. According to the invention, cells of an inactiviated culture or suspension cannot reproduce or divide. Preferably, the biocontrol compositions of the invention comprise inactivated cultures or suspensions of *B. casidae* strain 2.2N. More preferably, such biocontrol compositions comprise inactivated stationary cultures of strain 2.2N grown in a nitrogen-limited medium, such as TSM+S, or inactivated suspensions of strain 2.2N harvested from such cultures. *B. casidae* may be inactivated prior, or subsequent, to the harvest step.

*B. casidae* cells, cultures, suspensions, cell filtrates and cell fractions may be inactivated (i.e., treated such that any bacteria present no longer can divide or reproduce) using any method known in the art. Such method may comprise treating *B. casidae* cells, cultures, suspensions, cell filtrates and cell fractions with heat and/or chemicals to inactivate any live bacteria. Useful heat treatments include pasteurization, spray-drying at 150–200° C., and incubating a culture or suspension or cell-filtrate or cell fraction at about 80° C. to 100° C. for about 1 to about 15 minutes.

Cells, cultures, suspensions, cell filtrates and cell fractions of *B. casidae* also may be treated with various types of alcohols to inactivate any live bacteria. Alcohols that may be used to inactivate *B. casidae* include methanol, ethanol and isopropanol. In specific embodiments, the aforementioned materials are treated with isopropanol, which is added to a final concentration of about 70% (v/v), and the alcohol solution is incubated for about 15 min to about 1 hour at temperatures ranging from about 4° to 25° C. At the completion of the inactivation process, alcohol may be optionally removed from the solution or suspension by vacuum evaporation at 65° C.

Biocontrol compositions comprising *B. casidae* suspensions may also be prepared by harvesting *B. casidae* grown on solid media, and resuspending the harvested cells in buffers or fresh bacterial media. Such suspensions may be used directly in the preparation of biocontrol compositions or after *B. casidae* has been inactivated. Such suspensions can be treated using methods and conditions described above for the "inactivation" of liquid cultures of *B. casidae*.

The invention provides liquid biocontrol compositions comprising *B. casidae* cultures or suspensions that have combined cell and cyst concentrations of about $1 \times 10^3$ to about $3 \times 10^{11}$ cells and cysts per ml, preferably about $1 \times 10^6$ to about $3 \times 10^{11}$ cells and cysts per ml, and most preferably about $1 \times 10^8$ to about $3 \times 10^{17}$ cells and cysts per ml. The concentration of cells and cysts of *B. casidae* in liquid biocontrol compositions may be adjusted using methods known in the art, e.g., by diluting with buffers or bacterial media or by concentrating with filtration or centrifugation.

In yet additional embodiments, liquid biocontrol compositions of the invention comprise cell-free filtrates or cell fractions of *B. casidae* cultures or suspensions having cell and/or cyst concentrations described above. Cell-free filtrates or cell fractions may be prepared from such cultures and suspensions of live or inactivated *B. casidae* (prepared as described above) by standard methods such as centrifugation followed by filtration of the supernatant. In preferred embodiments, the cell-free filtrates or cell fractions are prepared from inactivated *B. casidae* cultures or suspensions which have been incubated for several days in media or buffer to accumulate the antimicrobial compounds extracellularly. The concentration of antimicrobial compounds present in the cell-free filtrates or cell fractions may be adjusted by diluting with buffers or media or by concentrating with vacuum evaporation or ultrafiltration.

In additional embodiments, liquid biocontrol compositions of the invention comprise spray- or freeze-dried cultures, cells (e.g., cell pastes), cell-free culture-filtrates, or cell- or culture-fractions. Spray drying can be performed at temperatures of 150° to 200° C. without loss of biocontrol activity.

In further embodiments, the liquid biocontrol compositions of the invention comprise solutions of antimicrobial preparations prepared as described in section 5.3. above.

As an important use of the liquid biocontrol compositions of the invention is for treatment of plants (discussed below) to protect against or treat microbial diseases, the biocontrol compositions may comprise additional ingredients known in the art that facilitate such treatments or enhance the effectiveness of such treatments. Such additional ingredients include, but are not limited to, antioxidants, dyes, detergents, salts, emulsifiers, surfactants, encapsulants (e.g., cellulose- and lignin-based gels), inert carriers (e.g., diatomaceous earth, vermiculite, and clay minerals), ultraviolet (UV) light-blocking agents, preservatives, and thickening agents (e.g., gelatin, polyethyleneglycol). Such additional ingredients should not be used at levels that would be phytotoxic to the plant species being treated and, preferably, also not inhibitory to *B. casidae* where live cultures or cells or cysts are being applied in the treatment.

5.4.2. Solid and Gel-encapsulated Biocontrol Compositions

Solid biocontrol compositions of the invention comprise solid carriers containing, or coated with, any of the following: live or inactivated *B. casidae*; antimicrobial compounds produced by *B. casidae*; and antimicrobial preparations of the invention. Numerous solid carriers are known in the art and may be used. They include, but are not limited to: activated charcoal, alginate, bone powder, calcium carbonate, cellulose, chitin, clay minerals (e.g., bentonite), dolomite, humus, insoluble phosphates (e.g., rock phosphate), peat, soil, talc, titanium dioxide, nut shells, crab shells, and lignins.

A solid biocontrol composition of the invention can be prepared by suspending a solid carrier in a culture or suspension of live or inactivated *B. casidae*, or a cell-free filtrate or cell fraction of a *B. casidae* culture or suspension, or a solution of an antimicrobial preparation of the invention; and drying the suspension under mild conditions, such as evaporation at room temperature or vacuum evaporation at 65° C. or lower. Preferred carriers for use in preparing solid biocontrol compositions are those which are not phytotoxic and, where live *B. casidae* is being carried, preferably non-bacteriocidal or non-bacteriostatic.

To enhance binding or absorption of *B. casidae* cells and/or cysts to a carrier, an adhesive or binding agent known in art may be added to the appropriate suspension prior to drying. Useful adhesives and binding agents include, but are not limited to, agar, gelatin, sugars, synthetic glue, and vegetable glue (e.g., gum arabic). The dried material is finely ground (i.e., at least 90% passing through 300 mesh) to produce a solid biocontrol composition.

In preferred embodiments, the solid biocontrol compositions are prepared with cultures or suspensions of live or inactivated *B. casidae* strain 2.2N.

A solid biocontrol composition of the invention also can be prepared by spray- or freeze-drying cultures, cells (e.g., cell pastes), cell-free culture-filtrates, or cell- or culture-fractions.

A biocontrol composition of the invention may comprise gel-encapsulated *B. casidae* cultures, cells, cysts, cell-free filtrates or cell fractions, or antimicrobial preparations of the invention. Such gel-encapsulated materials can be prepared by mixing a gel-forming agent (e.g., gelatin, cellulose, or lignin) with a culture or suspension of live or inactivated *B. casidae*, or a cell-free filtrate or cell fraction of a *B. casidae* culture or suspension, or a spray- or freeze-dried culture, cell, or cell fraction or in a solution of antimicrobial preparations of the invention; and inducing gel formation of the agent.

5.5. Methods for Prevention or Treatment of Microbial Diseases of Plants

The present invention also provides methods for treating and preventing microbial diseases of plants. The biocontrol methods of the invention generally comprise treating subject plants with one dose or several doses ("a regime") of a biocontrol composition of the invention. The methods of the invention may be administered prophylactically (prevention), before the appearance of any disease symptoms on subject plants or therapeutically (treatment), after disease symptoms have been detected.

The treatment with a biocontrol composition can be made directly onto a plant. In one embodiment, the plant is sprayed with a liquid biocontrol composition of the invention. Preferably, the liquid biocontrol composition comprises a culture or suspension of strain 2.2N, or cell-free filtrate, or spray- or freeze-dried material, or cell fraction thereof. More preferably, the liquid biocontrol composition comprises a culture or suspension of live cysts of strain 2.2N. In another embodiment, the plant is dusted with a solid biocontrol composition of the invention. Preferably, the solid biocontrol composition comprises live or inactivated cysts of strain 2.2N. The direct treatments are particularly effective in controlling air-borne microbial diseases.

The treatment with a biocontrol composition also can be made indirectly by application to the soil in the immediate vicinity of a plant or in the area in which a seed has been, or will be, planted. In one embodiment, the soil at the target site is irrigated with an aliquot of a liquid biocontrol composition of the invention. Preferably, the biocontrol composition comprises a culture or suspension of live strain 2.2N. In another embodiment, a plant seed is coated with a solid or gel biocontrol composition of the invention using methods known in the art (see, e.g., U.S. Pat. No. 4,798,723). Preferably, the solid or gel biocontrol composition comprises live strain 2.2N. In yet another embodiment, a solid or gel biocontrol composition of the invention is mixed into the target site. Such indirect treatments are particularly effective in controlling soil-borne microbial pathogens.

The effectiveness of treatment with a biocontrol composition may be determined by comparing the number of disease lesions appearing in treated and untreated plants that all have been infected with a microbial pathogen of interest. As used herein, an "effective" dose or regime of treatment with a biocontrol composition against a particular microbial pathogen is one whose application achieves at least 20%, preferably at least 50%, more preferably at least 80%, and most preferably at least 90%, disease control against that pathogen, as assessed using the method described in Section 6.3. An effective dose or regime may be achieved by adjusting the level of active ingredient(s) in the biocontrol composition and/or the amount or frequency of biocontrol compositions applied.

The biocontrol methods of the inventions may be beneficially used to prevent or treat a wide variety of microbial diseases of plants. Fungal diseases of plants that can be prevented, controlled or ameliorated by the methods of the invention include, but are not limited to, those caused by fungi in any of the following genera: Alternaria, Aspergillus, Botrytis, Cercospora, Cercosporidium, Erysiphe, Geotrichum, Mycosphaerella, Mucor, Penicillium, Phoma, Phytophthora, Plasmopora, Pseudopeziza, Puccinia, Pythium, Rhizoctonia, Rhizopus, Septoria, Sporothrix, Stemphylium, Trichophyton, and Verticillium. Bacterial diseases of plants that can be controlled or ameliorated by the methods of the invention include, but are not limited to, those caused by bacteria in any of the following genera: Pseudomonas, Erwinia and Xanthomonas.

The methods of the invention may be beneficially applied to preventing or treating fungal and bacterial diseases of a wide variety of agronomically important plants including, but not limited to: crop plants such as corn, soybean, wheat, rice, alfalfa, sorghum, peanut, tobacco, cotton, flax, safflower, oats, and canola; fruits and vegetables such as tomato, pepper, cucumber, lettuce, green beans, lima beans, peas, cantaloupe, musk melon, citrus fruits, grapes, and banana; and ornamentals and cut flowers such as geraniums, azaleas, roses, tulips, petunias, orchids, carnations, poinsettias, chrysanthemums; and conifers such as pine, yew, spruce. The present invention is more completely illustrated by the following non-limiting examples.

6. EXAMPLES

6.1. Isolation and Identification of *Burkholderia casidae*

6.1.1. Methods for Isolation of Predator Bacteria

6.1.1.1. Method One

Ten gram samples of a Hagerstown silty clay loam soil (pH 6.1), a Cazenovia silt loam soil (pH 7.0) collected in VAuburn, N.Y., a Dresden silt loam soil (pH 6.7) collected in Evansville, Wis., and a Dresden silt loam soil (pH 5.7) collected in Evansville, Wis. were placed in sterile 1 oz screw capped bottles. Soils were adjusted to 65% moisture-holding capacity and a suspension of *Micrococcus luteus* was added to yield $2.5 \times 10^7$ *M. luteus* cells (as colony-forming units) per gram dry weight of soil. The *M. luteus* suspension was prepared by collecting cells from a culture grown in 0.25% (w/v) Brain Heart Infusion Broth (BHIB) for 5 days at 27° C. Cells were washed three times in sterile tap water and suspended in a volume of sterile tap water equal to that of the culture. Bottles were incubated at 27° C. with caps loosened. After 1 and 2 weeks of incubation, *M. luteus* suspensions at a concentration of $7 \times 10^6$ cells per gram of dry soil were added to maintain the moisture level.

Survival of the *M. luteus* cells in the incubated soil samples was 11% after 1 week incubation and less than 0.1% at 3 weeks incubation.

After 3 weeks incubation, 0.1 ml of dilutions of the soil samples in water were spread lightly over lawns of *M. luteus* cells. Lawns of *M. luteus* were prepared on BHIB agar containing 0.25% (w/v) Brain Heart Infusion Broth and 1.5% (w/v) agar. Plates were inoculated with 0.2 ml of a water suspension of *M. luteus* cells prepared from a culture grown in 0.25% (w/v) BHIB for 5 days at 27° C. Plates were incubated 3 days at 27° C. to allow sufficient growth of *M. luteus* and then spread with dilutions of each soil sample.

Predator bacteria were identified as colonies surrounded by cleared zones, free from cells of *M. luteus*. Such colonies were isolated and characterized for predator activity.

Lysis of *M. luteus* cells was observed when suspensions of a predator bacteria were streaked perpendicularly across streaks of *M. luteus* on BHIB agar. At the point of intersection, the growth of predator bacteria moved progressively to the side of, and tracked along, the *M. luteus* streak. As a consequence, the *M. luteus* streak was covered with the growth of the predator bacteria and cells of *M. luteus* were lysed.

6.1.1.2. Method Two

Predator bacteria were isolated employing soil column slides. Washed cells of *M. luteus*, prepared as described in Section 6.1.1.1., were smeared on the surface of sterile glass slides. A glass ring 11 mm high by 25 mm in diameter was placed on the smear and the ring filled with soil. The soils were those described in Section 6.1.1.1. The soil was tamped lightly to ensure contact with the *M. luteus* smear. Moisture-holding capacity was adjusted to 65%, and incubation was at 27° C. in sterile petri dishes.

At the completion of incubation, excess soil was gently removed from the soil-column slides. For isolation of predator bacteria, the soil was gently removed to expose the slide surface where the *M. luteus* cells had been smeared. An inoculating loop that had been heated and plunged hot into agar was touched against this area and then streaked through a lawn of *M. luteus* prepared as described in Section 6.1.1.1.

When material from the soil column slides was streaked through the *M. luteus* lawn, colonies of predator bacteria appeared as those that caused lysis of *M. luteus* in their immediate vicinity.

6.1.1.3. Method Three

One-gram samples of a Hagerstown silty clay loam (pH 6.2), designated RS89, were placed in 18×150 mm screw cap tubes that also contained 10 ml of distilled water. The soil samples were sieved before use with a 3 mm pore-size sieve and 0.8 mg of L-glutamic acid (Sigma Chemical Co., St. Louis, Mo.) per gram of soil was added to the 10 ml water. The soil suspension in the tube was mixed thoroughly with a vortex mixer and then incubated with agitation for 24 hours at 28° C.

After incubation, the 10 ml of soil suspension plus 90 ml of sterile distilled water (i.e., 100-fold dilution of soil) was transferred to a sterile Waring blender head and blended 1 min. Further 10-fold dilutions were prepared from this blended 100-fold dilution. Soil dilutions were plated on Copper medium agar containing (0.25% (w/v) BHIB, 0.01% (w/v) $CuCl_2 \cdot 2\ H_2O$ and 1.5% agar (pH 6.5)).

Colonies of different morphologies appeared on Copper medium agar after 1 to 7 days incubation at 28° C. *B. casidae* colonies were white, opaque, raised, beehive-shaped, and about 2 to 4 mm in diameter. Predator bacteria, including *B. casidae*, could be demonstrated as follows. Putative predator bacteria were streaked near one edge of BHIB agar plates, and the plates were incubated for 24 hr at 28° C. A second streak of *Saccharomyces cerevisiae* or *M. luteus* was then inoculated on the plates as a streak perpendicular to, but not quite touching, the predator bacteria streak. The plates were then further incubated at 28° C. Predator bacteria were identified as those that produced zones of cleaning of *S. cerevisiae* or *M. luteus* up to 20 mm in width.

6.1.1.4. Method Four

Predator bacteria were isolated by plating dilutions of unfiltered percolation fluid from an *M. luteus*-treated soil column on MacConkey agar (Difco, Detroit, Mich.). Percolation fluid was collected from soil columns in the following manner. Twenty-five grams of soil (Table 1, infra) and 25 grams of sand were thoroughly mixed and placed in a soil percolation column in steps. A porous, plastic membrane support from a membrane filter apparatus was used to support he soil-sand mixture. A suspension of prey microorganism (e.g., *M. luteus*) was also added over and through the soil-sand column in steps. In step 1, a 10 ml portion of the suspension was poured over about one-third of the soil-sand mixture. In the second step, the second third of the soil-sand mixture was layered and 10 ml more of the cell suspension used to wet the soil. This procedure was repeated for the final third of the soil-sand mixture resulting in "saturation" of the soil-sand mixture with prey microorganism.

The inoculated soil column was incubated at 27° C. At various time intervals (usually 24 hr), 10 ml of sterile distilled water was added to the top of the column and samples of percolation fluid collected. Percolation fluid samples were spread, either undiluted or diluted, on the surface of MacConkey agar. *M. luteus* fails to grow on this medium and predator bacteria can be isolated and tested for predator activity as described in Section 6.1.1.1. or 6.1.1.2. and predator bacteria identified.

The soils that yielded predator bacteria are listed in Table 1 below.

TABLE 1

Soils Yielding Predator Bacteria.

| Soil | Location | Site | pH |
| --- | --- | --- | --- |
| Hagerstown Silty Clay Loam | State College PA | Grass | 6.1 |
| Cazenovia Silt Loam | Auburn NY | Garden | 7.0 |
| Dresden Silt Loam | Evansville WI | Garden | 6.7 |
| Webster Silty Clay Loam | Monona IA | Corn | 5.6 |
| Hagerstown Silty Clay Loam | State College PA | Grass | 5.3 |
| Tuxford Clay Loam | Weyburn SASK | Plain | 7.2 |
| Yorkton Loam | Watson SASK | Plain | 6.9 |
| Waitville Loam | Glaslyn SASK | Plain | 6.7 |

6.1.1.5. Method Five

A soil-plating procedure was employed to isolate predator bacteria. Plates were poured with 1.5% (w/v) Noble agar and allowed to solidify. To the surface of the agar was added 0.2 ml of an *Arthrobacter globiformis* (ATCC 8010) culture filtrate and 0.1 ml of a dilution in sterile tap water of the soil sample. The *A. globiformis* culture filtrate was prepared by inoculating BHIB and incubating with shaking for 3 days at 30° C. The pH of the broth increased to 8.7 during incubation. The cells were removed by centrifugation, and the supernatant culture medium was sterilized by filtration through a membrane filter of pore size 0.22 µm.

After 7 to 11 days incubation of the plates at 30° C., the plates were inspected for the presence of colonies having a "fried-egg" or "beehive" appearance. Detection and identification of such colonies required 20-fold magnification because of their small size (i.e., 0.1 to 0.5 mm diameter). These colonies were tested for predator activity as described in Section 6.1.1.1. or 6.1.1.2 and predator bacteria identified.

6.1.1.6. Method Six

The following soil-plating technique was also successfully used to isolate predator bacteria. In this method, a soil dilution was spread directly onto the surface of a modified Burk Azotobacter (BA) agar that lacks a carbon source and contains only a minimal nitrogen level. The BA agar medium comprised 0.08% $K_2HPO_4$, 0.02% $KH_2PO_4$, 0.02% $MgSO_4.7H_2O$, 0.01% $CaSO_4.2H_2O$, 0.000025% $NaMoO_4.2H_2O$, 0.00086% $Fe(NH_4)_2(SO_4)_2.12H_2O$, and 1.5% Noble agar.

After 7 to 11 days incubation of the plates at 30° C., the plates were inspected for the presence of colonies having a "fried-egg" or "beehive" appearance. Detection and identification of colonies required 20-fold magnification because of their small size (i.e., 0.1 to 0.5 mm diameter). Colonies were tested for predator activity as described in Section 6.1.1.1. or 6.1.1.2. and predator bacteria identified.

6.1.1.7. Method Seven

Predator bacteria also were isolated by a "baiting" technique that appears to operate on the basis of chemotaxis. Air-dried soil was passed through a 1.19 mm sieve, then placed to a depth of 3–4 mm in a sterile Petri dish (90 mm internal diameter). The soil was tamped lightly with the edge of a microscope slide to give a uniformly flat surface. About 2 ml of sterile distilled water was then added along the walls of the plate so the soil became moist but not flooded.

In a separate, sterile Petri dish, a 47 mm diameter membrane filter of 0.65 µm pore size was placed on a 8.5 cm circle of sterile Whatman No. 2 filter paper. To the membrane filter was added 0.2 ml of a washed suspension of *M. luteus* cells, prepared as described in Section 6.1.1.1. The suspension was spread over a 28 mm diameter area in the center of the filter.

The membrane filter was then transferred onto the soil surface with the side having the cells facing the soil and pressed onto the soil surface using a sterilized edge of a microscope slide. Each soil-filled Petri dish could hold 2 filters. The lids of the Petri dishes were placed on the filter-soil combination and plates sealed with tape and incubated right side up at 27° C. Cleared areas appeared on the filters within 2 to 3 days of incubation.

At various periods of incubation from 1 to 14 days, material from cleared areas on the filters (e.g., filter and bacteria) were removed with a sterile spatula and suspended in 5 ml sterile tap water. After mixing, a 2-fold dilution series was prepared in sterile tap water and 0.1 ml of the undiluted and diluted suspensions were spread on the surface of agar medium along with 0.1 ml of the washed *M. luteus* suspension prepared as described in Section 6.1.1.1. The media used were 1.5% (w/v) Noble agar or BHIB agar.

The plates were incubated 3 days at 27° C. and inspected for the appearance of colonies surrounded by cleared zones of *M. luteus* cells. Such predator colonies were picked and purified on BHIB agar, to ensure that non-obligate predator bacteria were recovered. Isolates were then tested for predator activity as described in Section 6.1.1.1. or 6.1.1.2. and predator bacteria identified.

6.1.2. Identification and Characterization of Strain 2.2N
6.1.2.1. The 16S rRNA Gene of Strain 2.2N A culture of strain 2.2N was grown in 10 ml TSM+S medium in a 125 ml Erlenmeyer flask with cotton stopper. The culture was inoculated with a single colony of strain 2.2N and incubated at 30° C. for 24 hours. The culture was aerated by rotation at 60 rpm. Following incubation, cells were harvested by centrifugation (5,000×G for 30 min at 4° C.). Genomic DNA was isolated using the Marmur method (i.e., Marmur, J. Mol. Biol. 3:208–218, 1961).

The 16S rRNA gene was amplified using PCR employing universal bacterial primers for the 16S rRNA gene. Two sets of primers were used to sequence the entire 16S rRNA gene. The forward primers were:

27f: 5'-AGA GTT TGA TCC TGG CTC AG-3' (SEQ ID NO:2)

704f: 5'-GTA GCG GTG AAA TGC GTA GA-3' (SEQ ID NO:4)

The reverse primers were:

1522r: 5'-AAG GAG GTG ATC CA (AG) CCG CA-3' (SEQ ID NO:3)

907r: 5'-CCG TCA ATT CCT TTG AGT TT-3' (SEQ ID NO:5)

The PCR amplification was carried out using one microgram of strain 2.2N DNA with 3.2 pmol each of a forward and a reverse primer.

The sequence of the amplified product was determined using an ABI Prism TM377 automated DNA sequencer following the instructions provided by the manufacturer. Taq DNA polymerase was used in DyeDeoxy™ terminator cycle sequencing reactions. All four termination reactions were performed in a single reaction and the products were loaded into a single lane of a polyacrylamide gel for separation. Real time detection of separated, individual fragments was achieved with laser scanning.

*B. casidae* appears to have five 16S rRNA operons. The DNA sequenced was a PCR product of genomic DNA generated by primers 27f and 1522r. The sequence covers position 27 through position 1522 (the numbers reflect the numbering of the *Escherichia coli* 16S rRNA gene) of one, and possibly all five, 16S rRNA genes. Thus, the sequence shown in FIG. 1 covers greater than 98% of 16S rRNA sequence (see FIG. 1; SEQ ID NO:1). A sequence alignment program produced by DNASTAR, Inc., (Madison, Wis.) was employed to analyze the 16S rRNA sequence and to resolve any ambiguities or errors in sequencing.

A general description of the amplified 16S rRNA gene sequence of strain 2.2N is summarized in Table 2, below.

TABLE 2

General Description of the amplified 16S rRNA Gene Sequence of Strain 2.2N

Total number of bases is 1495
% A = 25.35
% G = 31.57

TABLE 2-continued

General Description of the amplified 16S rRNA Gene Sequence of Strain 2.2N

% T = 20.13
% C = 22.94
% Ambiguous 0.00
% A + T = 45.48

Pairwise comparisons of 16S rRNA gene sequences between that of strain 2.2N and those of other bacteria were performed by "Clustal Analysis" employing DNASTAR. The results of the pairwise comparison of similarities of 16S rRNA gene sequences of strain 2.2N with that of other bacteria, particularly members of the genus Burkholderia, are presented in Table 3.

TABLE 3

Percent Similarity of Paired 16S rRNA Gene Sequences of Members of the Genus Burkholderia and *Escherichia Coli*

| | Bacterial Strains[a] | | | | | | | |
|---|---|---|---|---|---|---|---|---|
| | 2.2N | 23061 | 25418 | x80284 | 10248 | s55000 | R780 | X80724 |
| 2.2N | 100 | 88.8 | 93.0 | 94.6 | 94.5 | 94.1 | 86.3 | 71.7 |
| 23061 | 88.8 | 100 | 93.2 | 92.2 | 94.7 | 93.6 | 88.3 | 76.0 |
| 25418 | 93.0 | 93.2 | 100 | 93.2 | 95.3 | 93.7 | 87.8 | 75.4 |
| X80284 | 94.6 | 92.2 | 93.2 | 100 | 95.4 | 90.7 | 87.7 | 74.1 |
| 10248 | 94.5 | 94.7 | 95.3 | 95.4 | 100 | 95.5 | 88.8 | 75.2 |
| S55000 | 94.1 | 93.6 | 93.7 | 90.7 | 95.5 | 100 | 89.1 | 74.3 |
| R780 | 86.3 | 99.3 | 87.8 | 87.7 | 88.8 | 89.1 | 100 | 73.5 |
| X80724 | 71.7 | 76.0 | 75.4 | 74.1 | 75.2 | 74.3 | 73.5 | 100 |

[a]Bacterial strains: 2.2N, *B. casidae* strain 2.2N; 23061, *Burkholderia andropogonis*; 25418, *Burkholderia caryophylii*; X80284, *Burkholderia cepacia*; 10248, *Burkholderia gladioli*; S55000, *Burkholderia mallei*; R780, *Burkholderia solanacearum*; X80724, *Escherichia coli*.

The high degree of similarity of the 16S rRNA sequence of strain 2.2N with representatives of Burkholderia species indicates that strain 2.2N is a member of the genus Burkholderia.

6.1.2.2. Fatty Acid Composition of Strain 2.2N

A culture of strain 2.2N was streaked on TSM agar and incubated at 30° C. After 24 hour incubation, approximately 40 mg of cell material was harvested and cellular fatty acids extracted and transformed to methyl esters for gas chromatography (GC) analysis. Specifically, cell material was first saponified, then the cellular fatty acids were methylated, and then the methyl esters of the fatty acids extracted. Extracted fatty acid methyl esters of 9 to 20 carbons in length were identified and their percent composition was determined by GC analysis. Individual peaks were identified by retention time in comparison to those of a library of fatty acids, and the area under each peak measured.

The individual cellular fatty acids and percent composition of each, for strain 2.2N, are listed in Table 4.

TABLE 4

Cellular Fatty Acid Composition of Burkholderia spp. and *Burkholderia casidae* strain 2.2N

| Fatty Acid | A | B | C | D | E | F | G | H | I |
|---|---|---|---|---|---|---|---|---|---|
| C10:0 | 1 | — | — | — | — | — | — | — | ND |
| C12:0 | 4 | — | — | — | — | — | — | — | 0.8 |
| C13:1 | ND | ND | ND | ND | ND | ND | ND | ND | 0.7 |

TABLE 4-continued

Cellular Fatty Acid Composition of Burkholderia spp. and *Burkholderia casidae* strain 2.2N

| Fatty Acid | A | B | C | D | E | F | G | H | I |
|---|---|---|---|---|---|---|---|---|---|
| C14:0 | 1 | 5 | 4 | 4 | 4 | 4 | 5 | 5 | 2.9 |
| C15:0 | 1 | 1 | — | 1 | 1 | — | 2 | 1 | ND |
| C16:0 | 36 | 29 | 22 | 26 | 28 | 31 | 34 | 25 | 18.1 |
| C16:1 | 6 | 3 | 4 | 5 | 8 | 4 | 22 | 9 | 21.1 |
| C16:17,8 | ND | ND | ND | ND | ND | ND | ND | ND | ND |
| C17:0 | — | — | 3 | 1 | — | — | 1 | — | 0.4 |
| C17:CPA | 3 | 21 | 10 | 12 | 24 | 24 | 1 | 27 | 3.7 |
| C18:0 | 1 | 8 | — | 1 | — | 1 | — | 1 | 1.1 |
| C18:1 (9,10) | 2 | — | — | 1 | — | — | — | — | ND |
| C18:1 (11,12) | 22 | 8 | 20 | 18 | 12 | 8 | 18 | 13 | 39.2 |
| C19:CPA | 7 | 15 | 9 | 7 | 3 | 8 | — | — | 1.5 |
| 2-OH C12:0 | 5 | — | — | — | — | — | — | — | 0.7 |
| 2-OH C15:0 | ND | ND | ND | ND | ND | ND | ND | ND | ND |
| 2-OH C16:0 | — | 3 | 6 | 4 | 2 | 2 | 1 | 1 | 0.5 |
| 2-OH C16:1 | — | 1 | 3 | 1 | 5 | 1 | 1 | 5 | 0.7 |
| 2-OH C18:1 | — | 1 | 3 | 2 | 4 | 2 | 4 | 4 | 1.1 |
| 2-OH C19:CPA | — | 2 | 2 | 2 | — | 2 | — | — | ND |
| 3-OH C10:0 | 3 | — | — | — | — | — | — | — | ND |
| 3-OH C12:0 | 8 | — | — | — | — | — | — | — | ND |
| 3-OH C14:0 | — | 4 | 6 | 6 | 9 | 5 | 9 | 4 | 4.2 |
| 3-OH C16:0 | — | 6 | 8 | 8 | — | 8 | — | — | 3.4 |

A = *P. aruginosa*
B = *B. cepacia*
C = *B. mallei*
D = *B. pseudomallei*
E = *B. caryophilii*
F = *B. gladoli*
G = *B. pickettii*
H = *B. solanacearum* and
I = *B. casidae* strain 2.2N
The values shown in the table are in percent of all the fatty acids identified in the GC analysis.
ND = not detected Table 4 also contains data for fatty acids and their percent composition in cells of *Burkholderia cepacia, Burkholderia mallei, Burkholderia pseudomallei, Burkholderia caryophyli, Burkholderia gladoli, Burkholderia solanacearum,* and *Burkholderia pickettii*. The data were obtained from Yabuuchi et al., 1992, Microbiol. Immunol. 36:1251–1275.

The cellular fatty acid profile of strain 2.2N differs from representatives of other Burkholderia species in having a significantly lower percentage of C16:0 fatty acid and significantly higher percentages of C16:1 and C18:1 (11,12) fatty acids.

Since strain 2.2N has a unique cellular fatty acid profile, not displayed by representatives of any known species of Burkholderia, it is, therefore, a representative of a new Burkholderia species.

6.1.2.3. Carbon Utilization by Strain 2.2N

Fifty-four substrates were tested to identify those which strain 2.2N uses as carbon and energy sources. Substrate utilization was determined using the API50 CH test (bioMerieux S.A., Marcy-l'Etiole, France) following the instructions provided by the manufacturer. The results of that determination are listed in Table 5.

TABLE 5

Substrate Utilization Patterns of Burkholderia spp. and Strain 2.2N

| | Burkholderia species | | | | | | | | |
|---|---|---|---|---|---|---|---|---|---|
| Substrate | cepacia | marginata | allicola | caryophila | solanacearum | pickettii | gladioli | mallei | casidae 2.2N |
| 2-ketogluconate | + | + | + | + | − | + | + | − | − |
| 5-ketogluconate | + | ND | ND | + | − | − | + | ND | − |
| a-methyl-D-glucoside | ND | ND | ND | ND | ND | ND | ND | ND | − |
| a-methyl-D-mannoside | − | ND | ND | − | − | − | − | − | − |
| adipate | + | + | + | − | − | + | + | + | + |
| adonitol | + | + | + | − | − | − | + | ND | − |
| amygdalin | + | ND | ND | − | − | − | − | ND | − |
| arbutin | + | ND | ND | − | − | − | − | ND | − |
| b-methyl-D-xyloside | ND | ND | ND | ND | ND | ND | ND | ND | ND |
| caprate | + | + | + | − | − | − | + | − | + |
| cellobiose | + | + | + | + | − | * | + | + | − |
| citrate | + | + | + | + | ND | + | ND | ND | − |
| D-arabinose | + | + | + | + | − | − | + | + | − |

TABLE 5-continued

Substrate Utilization Patterns of Burkholderia spp. and Strain 2.2N

| Substrate | cepacia | marginata | allicola | caryophila | solanacearum | pickettii | gladioli | mallei | casidae 2.2N |
|---|---|---|---|---|---|---|---|---|---|
| D-arabitol | + | ND | ND | ND | − | − | + | + | − |
| D-fucose | + | + | + | + | − | − | + | + | + |
| D-lyxose | + | ND | ND | ND | ND | ND | ND | ND | ND |
| D-tagatose | + | ND | ND | ND | − | − | + | ND | − |
| D-turanose | ND | ND | ND | ND | − | ND | − | ND | − |
| D-xylose | + | + | + | + | − | + | + | + | − |
| dulcitol | + | ND | ND | ND | − | − | + | ND | − |
| erythritol | − | − | − | − | − | − | − | − | − |
| esculin | + | ND | ND | − | − | − | − | − | + |
| fructose | + | + | + | + | + | + | + | + | + |
| galactose | + | + | + | + | − | + | + | + | + |
| gentiobiose | ND | ND | ND | ND | ND | ND | ND | ND | ND |
| gluconate | + | + | + | + | ND | + | ND | ND | + |
| glucose | + | + | + | + | − | + | + | + | + |
| glycerol | + | + | + | + | + | + | + | + | − |
| glycogen | − | ND | ND | ND | − | − | − | ND | − |
| inositol | + | + | + | + | − | − | + | + | − |
| inulin | − | − | − | − | − | − | − | − | − |
| L-arabinose | + | + | + | + | − | + | + | − | − |
| L-arabitol | + | ND | ND | ND | − | − | − | ND | − |
| L-fucose | + | ND | ND | ND | − | − | + | ND | − |
| L-xylose | ND | ND | ND | ND | − | ND | − | ND | − |
| lactose | − | − | − | − | − | − | − | − | − |
| malate | + | + | + | + | − | + | + | − | − |
| maltose | − | − | − | − | − | − | − | − | − |
| mannitol | + | + | + | + | − | − | + | + | + |
| mannose | + | + | + | + | − | − | + | + | + |
| melezitose | − | ND | ND | ND | − | − | − | − | − |
| mellibose | − | ND | ND | ND | − | − | − | − | + |
| N-acetyl-glucosamine | + | ND | ND | ND | + | + | + | + | + |
| phenylacetate | + | + | + | + | − | − | + | + | + |
| raffinose | − | ND | ND | ND | − | − | − | − | − |
| rhamnose | − | − | − | + | − | − | − | − | − |
| ribose | + | ND | ND | ND | − | − | + | − | − |
| salicin | + | + | + | + | − | − | − | − | − |
| sorbitol | + | + | + | + | − | − | + | + | − |
| sorbose | ND | ND | ND | ND | ND | ND | ND | ND | − |
| starch | − | − | − | − | − | − | − | ND | − |
| sucrose | + | + | + | + | + | − | − | + | + |
| trehalose | + | + | + | − | − | − | + | + | − |
| xylitol | + | ND | ND | ND | − | − | + | ND | − |

Table 5 also lists substrates used as carbon and energy sources by strains of Burkholderia cepacia, Burkholderia marginata, Burkholderia allicola, Burkholderia caryophyli, Burkholderia solanacearum, Burkholderia pickettii, Burkholderia gladoli, and Burkholderia mallei. The data were obtained from Ballard et al., 1970, J. Gen. Microbiol. 60:199–214; Ralston et al., 1973, Int. J. System. Bacteriol. 23:15–19; Palleroni and Holmes, 1981, Int. J. System. Bacteriol. 31:479–481; Yabuuchi et al., 1992, Microbiol. Immunol. 36:1251–1275; and Bevivino et al., 1994, Microbiol. U.K. 140:1069–1077.

The pattern of carbon and energy sources utilized by strain 2.2N is unique among members of the genus Burkholderia. Based on the lack of any significant degree of similarity between the patterns of substrate utilization of other Burkholderia species and that of strain 2.2N, it was concluded that strain 2.2N is a representative of a new Burkholderia species.

6.1.2.4. Cultural, Biochemical, and Enzymatic Characteristics of Strain 2.2N

Cultural, biochemical, and enzymatic activities of strain 2.2N were determined using the API-NFT test (bioMerieux S.A., Marcy-l'Etiole, France) following the instructions provided by the manufacturer.

The results of the API-NFT test for strain 2.2N are shown in Table 6. Table 6 also contains data for corresponding cultural, biochemical, and enzymatic activities of strains of Burkholderia cepacia, Burkholderia mallei, Burkholderia pseudomallei, Burkholderia caryophyli, Burkholderia gladoli, Burkholderia pickettii, and Burkholderia solanacearum. The data were obtained from Ballard et al., 1970, J. Gen. Microbiol. 60:199–214, Ralston et al., 1973, Int. J. System. Bacteriol. 23:15–19; Palleroni and Holmes, 1981, Int. J. System. Bacteriol. 31:479–481; Yabuuchi et al., 1992, Microbiol. Immunol. 36:1251–1275;, and Bevivino et al., 1994, Microbiol. U.K. 140:1069–1077.

TABLE 6

Cultural, Biochemical, and Enzymatic Characteristics of B. casidae strain 2.2N and Burkholderia spp.

| Character | A | B | C | D | E | F | G | H |
|---|---|---|---|---|---|---|---|---|
| Growth at 41° C. | + | − | + | − | − | + | − | + |
| Yellow Pigment | + | − | − | − | − | + | − | − |
| NO$_3$ to NO$_2$ | − | + | + | + | − | + | + | + |
| Urease | − | − | − | − | − | + | + | − |
| Esculin Hydrolysis | + | − | − | − | − | − | − | + |
| Gelatin Hydrolysis | + | − | − | − | + | + | + | + |
| Arginine Dihydrolase | − | + | + | − | − | − | − | − |
| Cytochrome Oxidase | − | + | + | − | + | + | + | − |

TABLE 6-continued

Cultural, Biochemical, and Enzymatic Characteristics of *B. casidae* strain 2.2N and Burkholderia spp.

| Character | A | B | C | D | E | F | G | H |
|---|---|---|---|---|---|---|---|---|
| Indole Formation | – | – | – | – | – | – | – | + |

A = *B. Cepacia*
B = *B. mallei*
C = *B. pseudomallei*
D = *B. caryophilii*
E = *B. gladoli*
F = *B. pickettii*
G = *B. solanacearum*
H = *B. casidae* strain 2.2N.

Strain 2.2N displays a unique pattern of cultural, biochemical, and enzymatic activities that is not shown by any other members of the genus Burkholderia. Based on the lack of any significant degree of similarity between the patterns of cultural, biochemical, and enzymatic activities of representatives of other Burkholderia species and that of strain 2.2N, it was concluded that strain 2.2N is a representative of a new species of Burkholderia.

6.1.2.5. Antibiotic Susceptibility of Strain 2.2N

The susceptibility of strain 2.2N to various different antibiotics was tested employing the Sceptor Pseudomonas/Resistant MIC Panel (Becton-Dickinson, Sparks, NV) following the instructions of the manufacturer.

The susceptibility or resistance of strain 2.2N to antibiotics is displayed in Table 7. Strain 2.2N is resistant to most antibiotics commonly used to treat Pseudomonas spp. infections.

TABLE 7

Minimal Inhibitory Concentrations of Antibiotics Against B. casidae strain 2.2 N.

| Antibiotic | Minimal Inhibitory Concentration[1] |
|---|---|
| Cefotaxime | 64 micrograms/ml |
| Ceftizoxime | 16 micrograms/ml |
| Ceftazimine | 8 micrograms/ml |
| Ceftriaxone | 128 micrograms/ml |
| Imipenem | 16 micrograms/ml |
| Trimethoprim/Sulfamethoxazole | 4/76 micrograms/ml |
| Amikacin | >64 micrograms/ml |
| Cefoperazone | >16 micrograms/ml |
| Gentamycin | >16 micrograms/ml |
| Tetracycline | >8 micrograms/ml |
| Tricarcillin/Clavulinic Acid | >128/2 micrograms/ml |
| Tobramycin | >16 micrograms/ml |

[1]The minimal inhibitory concentration (MIC) is the lowest concentration of antibiotic that inhibits growth of strain 2.2N. Where the > sign is used, it indicates that strain 2.2N grew at the highest concentration of antibiotic tested. Thus, the MIC is higher than the indicated concentration.

6.2. Production and Assay of Antimicrobial Compounds Produced by *Burkholderia casidae*

6.2.1. Growth of Strain 2.2N

A single colony of strain 2.2N was picked and used to inoculate 10 ml of TSM+S medium. The inoculum culture was incubated 18 hours at 30° C. and refrigerated. It could be stored for up to 2 weeks prior to use as inoculum.

Test cultures were always assayed immediately following incubation and growth. However, antimicrobial compounds in the culture were stable for over 2 months storage, in a refrigerator (4° C.) or at room temperature, and their activity may be assayed at any time during that period.

6.2.2. Fractionation of Strain 2.2N Culture

In addition to whole cultures designated as "culture", and cell-free culture medium in which strain 2.2N had grown, antimicrobial preparations were made from strain 2.2N culture, and all were assayed for antimicrobial activity.

Production cultures of strain 2.2N to be used for dose-response measurements consisted of either 250 ml of TSM+S medium in a screw-cap 1-liter Erlenmeyer flask (flask culture) or 1,000 ml of TSM+S medium in a 2-liter fermenter (fermenter culture). Production cultures were inoculated with a 1:100 dose of starter culture (e.g., 2.5 ml of starter culture per 250 ml of fresh medium) and incubated 24 hours at 30° C. with aeration by rotation (60 rpm).

Several different materials were prepared from the production culture and tested for inhibitory activity against a number of fungi.

A fraction of a production culture was centrifuged (5,000×G for 30 min at 4° C.) and the supernatant liquid collected. A portion of the supernatant, spent medium was filtered through a 0.22μ pore size filter. This material was designated "Filtrate." A second portion of the supernatant, spent medium was heated to 80° C. for 5 minutes. This material was designated "Pasteurized."

The pellet from the centrifugation of culture was suspended in a volume of sterile distilled water equal to that of the original sample and resuspended. That fraction was designated "Cells".

Antimicrobial preparations were made from the production culture following procedures described in Section 6.5.1., below. The preparations were dissolved in buffer. This material was designated "Fungicide."

Another material tested was simply an untreated sample of the production culture. This material was designated "Culture."

6.2.3. Growth of Target Microorganisms 6.2.3.1. Yeasts

Single colonies of *S. cerevisiae, C. albicans,* or *C. neoformans* were picked and used to inoculate 20 ml of BHIM. The cultures were incubated 18 hours at 30° C. with shaking. Inoculum cultures grown in such a manner could be refrigerated for up to 2 weeks prior to use in activity assay.

A single colony of *S. cerevisiae* was picked and used to inoculate 10 ml of BHIM. The inoculum culture was incubated 18 hours at 30° C. with shaking and refrigerated. It could be stored for up to 2 weeks before use in assay.

6.2.3.2. *Micrococcus luteus*

A single colony of *M. luteus* was picked and used to inoculate 10 ml of BHIM. The culture was incubated 18 hours at 30° C. with shaking and refrigerated. It could be stored for up to 2 weeks prior to use in activity assay.

6.2.3.3. *Staphylococcus aureus*

A single colony of *S. aureus* was picked and used to inoculate 10 ml of BHIM. The inoculum culture was incubated 18 hours at 30° C. and refrigerated. It could be stored for up to 2 weeks prior to use in activity assay.

6.2.3.4. *Aspergillus niger*

A single colony of *A. niger* was picked and used to inoculate the surface of solid medium consisting of BHIM agar. The plate was incubated at 30° C. for 5 days, or until spore formation was evident from the black spores. Spores were harvested from the agar by adding 5 ml of water to the agar surface of the medium and gently dislodging the spores by repeatedly passing the side of a sterile glass rod over the surface. The spore-laden liquid was collected using a pipette and suspensions of single spores prepared by, first, a low speed centrifugation (1,000×G for 5 min at room temperature) to remove pelleted debris and, second, by a high speed centrifugation (5,000×G for 30 min at room temperature). The pelleted spores were collected, washed twice in distilled water, and resuspended in medium prior to use in activity assay.

6.2.3.5. Botrytis cinerea

A single colony of *B. cinerea* was picked and used to inoculate the surface of solid medium consisting of 20% (v/v) V8 Juice™ containing 0.25% (w/v) CaCO$_3$ and 1.5% (w/v) agar. The plate was incubated at room temperature for 5 days, or until spore formation was evident from the gray spores. Spores were harvested and prepared as described above for collection of *A. niger* spores.

6.2.3.6. Septoria nodorum

A single colony of *S. nodorum* was picked and used to inoculate the surface of solid medium consisting of 20% (v/v) V8 Juice™ containing 0.25% (w/v) CaCO$_3$ and 1.5% (w/v) agar. The plate was incubated at room temperature for 5 days, or until spore formation was evident from the gray spores. Spores were harvested and prepared for use in activity assay following procedures described above for collection of *A. niger* spores.

6.2.4. Activity Assay

One-tenth strength Brain Heart Infusion Broth containing 0.7% (w/v) agar, designated BHIM top agar, was prepared and sterilized by autoclaving and dispensed into 3 ml volumes in 13x100 mm tubes and cooled to 45° C. One-tenth ml of an inoculum culture or spore suspension of each prey microorganism was added to 3 ml of 45° C. BHIM top agar, mixed and poured over the surface of agar medium made up of BHIM or a medium composed of 20% (v/v) V8 Juice™, 0.25% CaCO$_3$ and 1.5% (w/v) agar. The later agar medium is used for activity for assays using *B. cinerea* or *S. nodorum* as prey microorganism. Immediately, or within 1 hour, 10 µl samples of the test material (see Section 6.2.2.) were spotted on the surface of the test plates and allowed to air dry. Plates were incubated at 30° C. and examined at hourly intervals for the appearance of zones of inhibition in the lawns of prey microorganism surrounding the spots of the test material. As control, 10 µl of sterile TSM was spotted on each lawn. Inhibitory activity of the test materials was assessed by measuring the diameter (mm) of the zones of inhibition of prey growth surrounding the spots of the test material.

6.2.5. Results

There was no inhibition of the prey microorganisms where 10 µl of the sterile TSM (control) had been spotted. Though there was growth of strain 2.2N cells in the centers of the zone of inhibition of spotted cultures or cells, there was no growth of cells in the zones of inhibition of the "Filtrate" or the "Pasteurized" materials. The inhibitory activity of the different types of sample material are shown in Tables 8 and 9, below.

TABLE 8

Inhibitory activity of strain 2.2N Culture, Filtrate and Cells.

| | Zone of Inhibition (mm ± std. dev.) | | | |
|---|---|---|---|---|
| Sample | No. of Trials | S. cerevisiae | No. of Trials | M. luteus |
| Culture | | 16.8 ± 1.2 | 1 | 17.0 |
| Filtrate | 8 | 9.9 ± 3.1 | 1 | 13.0 |
| Cells | 8 | 14.0 ± 2.3 | 1 | 17.0 |

TABLE 9

Inhibitory Activity of Materials Prepared From Strain 2.2N Culture.

| | Culture | Pasteurized | Filtrate | Fungicide |
|---|---|---|---|---|
| S. cerevisae | 17 ± 3.1[a] (519) | 11 ± 3.1 (57) | 10 ± 3.2 (18) | 13 ± 3.8 (49) |
| C. albicans | 15 ± 2.6 (12) | 10 ± 1.0 (4) | 8 ± 0.0 (1) | 8 ± 3.3 (5) |
| C. neoformans | 20 ± 3.5 (16) | 11 ± 1.0 (3) | 8 ± 0.7 (2) | 9 ± 2.8 (5) |
| A. niger | 22 ± 4.8 (36) | 12 ± 5.0 (5) | 12 ± 0.7 (2) | 13 ± 5.3 (42) |
| B. cinerea | 37 ± 0.0 (2) | ND[b] | ND | 13 ± 3.5 (2) |
| S. nodorum | 27 ± 6.2 (5) | ND | ND | 22 ± 1.4 (2) |
| M. luteus | 18 ± 3.0 (400) | 9 ± 3.3 (4) | 12 ± 4.7 (6) | 14 ± 5.7 (9) |
| M. smegmatis | 21 ± 3.4 (13) | ND | ND | 13 ± 0.7 (2) |

[a]The values are diameters of zones of inhibition with standard deviations. The numbers in parenthesis represent the number of samples tested.
[b]Not determined.

6.2.6. Effect of Growth Conditions on Production of Antimicrobial Compounds The effect of different media conditions and growth conditions on the production of antimicrobial activity was examined. Strain 2.2N was grown using conditions described in Table 10. The inhibitory activity of 2.2N cultures grown under the different conditions was assayed as described in Section 6.2.4.

The results, as shown in Table 10, indicated that cultures grown at 37° C., or anaerobically, produced lower levels of anti-fungal and antibacterial compounds, and that cultures grown in medium supplemented with ammonium or sulfate produced relatively more antibacterial than anti-fungal compounds.

TABLE 10

Influence of Medium and Culture Conditions Production of Antimicrobial Compounds by Strain 2.2N.

| Culture Medium[a] | No. of Trials | Diameter (mm) of Zone of Inhibition | | |
|---|---|---|---|---|
| | | S. cerevisiae | M. luteus | S. aureus |
| Standard | 6 | 18.5 | 18.5 | 10.0 |
| Std + NH4 | 1 | 18.0 | 22.0 | N.T. |
| Std + SO4 | 1 | 18.0 | 21.0 | N.T. |
| Std + EDTA | 1 | 17.0 | 17.0 | N.T. |
| Std + Metals | 1 | 18.0 | 19.0 | N.T. |
| Std + PO4 | 1 | 18.0 | 18.0 | 12.0 |
| Std − Buffer | 1 | 18.0 | 18.0 | 11.0 |
| Std + Tris | 1 | 18.0 | 18.0 | 13.0 |
| Std @ 37° C. | 1 | 11.0 | 17.0 | N.T. |
| Std − Air | 1 | 16.0 | 16.0 | N.T. |

[a]Standard (Std) refers to medium and conditions described in Section 6.2.1. for the growth of strain 2.2N; Std + NH4 = medium supplemented with 0.1 M NH$_4$Cl; Std + SO$_4$ = medium supplemented with 0.1 M Na$_2$SO$_4$; Std + EDTA = medium supplemented with 0.1 mM Na$_2$EDTA; Std + Metals = medium supplemented with 0.1 mM Mn$^{+2}$, Mg$^{+2}$, Zn$^{+2}$, and Ca$^{+2}$; Std + PO$_4$ = medium supplemented with 0.1 M PO$_4$ buffer (pH 7.0); Std − Buffer = medium without any PO$_4$ buffer; Std + Tris = medium supplemented with 0.1 M Tris buffer (pH 7.0); Std @ 37° C. = culture grown at 37° C.; Std − air = grown without aeration; N.T. = not tested.

6.3. Biocontrol Activity of *Burkholderia casidae*

6.3.1. Growth of Strain 2.2N

Production culture of strain 2.2N was prepared as described in Section 6.2.1., above.

6.3.2. Biocontrol Activity Assay

Biocontrol activity of strain 2.2N was assessed by placing fourteen plants (two to three plants per treatment) in a tray, and applying diluted or undiluted production culture of strain 2.2N with a hand-held sprayer. The activity of antimicrobial preparations prepared as described in Section 6.5. was also assayed. This material was designated as "Fungicide". Doses of the Culture and Fungicide tested included: undiluted (1×), one-third diluted (⅓×), one-tenth diluted (¹⁄₁₀×), one-thirtieth diluted (¹⁄₃₀×), one-hundredth diluted (¹⁄₁₀₀×), one-three-hundredth diluted (¹⁄₃₀₀×), and on-one-thousandth diluted (¹⁄₁,₀₀₀×). Plants were sprayed with each of these preparations until thoroughly wet. These are referred to as "treated" plants. Several plants were not sprayed. They served as untreated disease controls. Following spraying, plants were placed in separate trays, one for each fungal disease and allowed to air-dry for one to two hours.

Biocontrol activity of the Culture and Fungicide were tested against various fungal diseases of wheat, tomato, grape, rice, banana, peanut and pepper. Wheat plants were inoculated with *Erysiphe graminis* by shaking infected plants containing sporulating lesions over trays of strain 2.2N treated and untreated (control) plants. All other fungal inoculations were carried out by spraying the plants with a suspension of fungal spores.

The spore inoculated plants were placed in humidity chambers set at temperatures conducive to the development of each fungal disease. In addition to the untreated control plants that were inoculated with fungal spores, plants that were both untreated and uninoculated were included to provide disease-free controls.

All plants (i.e., uninoculated, inoculated, and inoculated and treated) were evaluated by visually estimating the level of disease control. The plants inoculated with fungi only were assigned a rating of 0%. Untreated and uninoculated plants were assigned a rating of 100%. These were used as comparison standards. Plants showing no disease lesions were given a rating of 100%. Plants with intermediate levels of disease were assigned appropriate intermediate values between 0 and 100%. Replicate plants were visually averaged and one disease rating was assigned for each treatment for each disease. Uninoculated plants that were treated with 2.2N were also observed for effects of the treatments other than disease control (e.g., phytotoxicity).

These assays also compared the activity of the Culture and Fungicide preparations (see above) in controlling *Botrytis cinerea* infection of geranium with that of a chemical fungicide Rovral® 50 WP (iprodine). The Rovral® was dissolved to 1 lb/100 gal in an aqueous solution of 5% acetone, 0.25% Triton X-155, and applied by spraying as described above for 2.2N Culture and Fungicide preparations.

6.3.3. Results of Biocontrol Activity Assays

The results shown in Table 11 (below) list the average (±standard deviation) disease control activity of undiluted production cultures of strain 2.2N. Tomato, grape, pepper and wheat plants treated with strain 2.2N and not inoculated with pathogens showed no disease or phytotoxic symptoms.

TABLE 11

Biocontrol Activity of Strain 2.2N

| Fungus | Plant | Trials | Percent Disease Control |
|---|---|---|---|
| *Phytophthora infestans* | Tomato | 8 | 70 ± 19 |
| *Alternaria solani* | Tomato | 8 | 64 ± 28 |
| *Plasmopora viticola* | Grape | 8 | 60 ± 42 |
| *Botrytis cinerea* | Pepper | 8 | 100 ± 0 |
| *Septoria nodorum* | Wheat | 8 | 96 ± 7 |
| *Puccinia recondita* | Wheat | 8 | 63 ± 42 |

Tables 12 and 13, below, show the activity of undiluted and diluted 2.2N Culture and Fungicide preparations in controlling various fungal diseases of tomato, rice, pepper, wheat, banana and peanut. The results show that the 2.2N Culture and Fungicide preparations can be diluted 3-fold and still exert good biocontrol activity against fungal infections caused by *Phytophthora infestans*, *Pyricularia oryzae*, *Botrytis cinerea*, *Septoria nodorum*, *Puccinia recondita*, *Septoria tritici*, *Mycospharella fijiensis*, *Cerospora arachidocola*, and *Cercosporidium personatum*.

TABLE 12

Antifungal activity of Culture and Fungicide preparations

| | | Percent Disease Control | | | |
|---|---|---|---|---|---|
| | | Culture | | Fungicide | |
| Fungus | Host Plant | 1 X | 0.33 X | 1 X | 0.33 X |
| *Phytophthora intestans* | tomato | 90 | 70 | 53 | 23 |
| *Pyricularia oryzae* | rice | 100 | 50 | 93 | 17 |
| *Botrytis cinerea* | pepper | 100 | 100 | 100 | 53 |
| *Septoria nodorum* | wheat | 100 | 99 | 92 | 63 |
| *Puccinia recondita* | wheat | 100 | 99 | 96 | 87 |

TABLE 13

Antifungal activity of Culture and Fungicide preparations.

| | | Percent Disease Control | | | |
|---|---|---|---|---|---|
| | | Culture | | Fungicide | |
| Fungus | Host Plant | 1 X | 0.33 X | 1 X | 0.33 X |
| *Septoria tritici* | wheat | 70 | 58 | 75 | 63 |
| *Mycospharella fijiensis* | banana | 100 | 91 | 100 | 100 |
| *Cerospora arachidocola* | peanut | 91 | 84 | 92 | 85 |
| *Cercosporidium personatum* | peanut | 91 | 84 | 92 | 85 |

Comparisons with the chemical fungicide Rovral® shows that both the 2.2N Culture and Fungicide preparations have good activity in controlling *B. cinera* infection of geranium (Table 14).

TABLE 14

Percent control of B. cinerea infection of geraniums treated with strain 2.2N Culture and Fungicide preparations and Rovral ®.

| | Percent Disease Control | | | | |
|---|---|---|---|---|---|
| dilution | X | 1/3 X | 1/10 X | 1/30 X | 1/100 X |
| Culture | 85 | 75 | 15 | 6 | 0 |
| Fungicide | 86 | 85 | 73 | 25 | 0 |
| concentration | 600 ppm | 200 ppm | 60 ppm | 20 ppm | 6 ppm |
| Rovral ® | 96 | 81 | 35 | 0 | 0 |

The results of Table 15, below, show that production cultures of strain 2.2N can be diluted 10 to 30 fold and still exert significant biocontrol activity against plant fungal pathogens.

TABLE 15

Titration of Inhibitory Activity in 2.2N Cultures

| | | Percent Disease Control | |
|---|---|---|---|
| Treatment | Dilution of Production Culture | Pepper inoculated with B. cinerea | Wheat inoculated with S. nodorum |
| Flask Culture | 1 X | 92 | 99 |
| | 1/3 X | 92 | 94 |
| | 1/10 X | 80 | 74 |
| | 1/30 X | 76 | 49 |
| | 1/100 X | 61 | 22 |
| | 1/300 X | 9 | 4 |
| | 1/1,000 X | 4 | 0 |
| Fermentor Culture | 1 X | 93 | 100 |
| | 1/3 X | 75 | 97 |
| | 1/10 X | 75 | 85 |
| | 1/30 X | 69 | 60 |
| | 1/100 X | 64 | 37 |
| | 1/300 X | 29 | 22 |
| | 1/1,000 X | 4 | 10 |

6.4. Biocontrol Activity of Spray-dried Cells of Burkholderia casidae

6.4.1. Growth of Strain 2.2 N

Production culture of strain 2.2 N was prepared as described in Section 6.2.1., above.

6.4.2. Preparation of Cell Paste

The culture was passed through a Sharples centrifuge and the cells harvested from the walls of the chamber. The resulting cell paste had approximately 32% solids and a pH of 4.5. The mean particle size was 0.9 microns.

6.4.3. Spray Drying

The cell paste, prepared as described in section 6.4.2, was diluted to about 28.5% solids and spray dried at a dried inlet temperature of 170° C. and outlet temperature of about 100° C. The flow rate of the feedstock (i.e., cell paste) was approximately 85 ml per minute. The main chamber yield of the dry product from the feedstock was about 21% and from the cyclone about 28% (total recovery equal to about 49% of feedstock). The main chamber and cyclone collected products were combined for physical and anti-microbial assays. The dried product moisture content was about 5% and the particle size mean was about 0.85 microns.

6.4.4. Biocontrol Activity Assay

One gram of the spray-dried powder was dissolved in 100 ml of water (1×concentration). Doses of the spray-dried Material tested included: undiluted (1 gm in 100 ml=1×), one-tenth diluted (1/10×), one-hundredth diluted (1/100×), and one-three-hundredth diluted (1/300×). Biocontrol activity of the spray-dried material and dilutions were assessed as described in Section 6.3.2., above.

6.4.5. Results of Biocontrol Activity Assays

The results of measurement of the anti-fungal activity of the spray-dried material produced from cultures of B. casidae strain 2.2 N are displayed in Table 16 (below). Table 12 lists the percent disease control of the undiluted and diluted spray-dried material and of the culture used to prepare the spray-dried material.

TABLE 16

Biocontrol Activity of Spray-Dried Cells of B. casidae strain 2.2N

| | | Disease Control (%) | | | | |
|---|---|---|---|---|---|---|
| Formulation | Sample | Pi | Po | Bc | Sn | Pr |
| Spray Dried | 1 X | 95 | 90 | 100 | 100 | 100 |
| | 1/10 X | 80 | 75 | 100 | 90 | 65 |
| | 1/100 X | 75 | 0 | 100 | 0 | 0 |
| | 1/300 X | 0 | 0 | 0 | 0 | 0 |

Pi = *Phytophthora infestans*; Po = *Pyricularia oryzae*; Bc = *Botrytis cinerea*; Sn = *Septoria nodorum*; Br = *Puccinia recondita*

The results show that the spray-dried material prepared from cells harvested from a culture of B. casidae strain 2.2 N can be diluted up to 100-fold and still exert complete biocontrol activity against fungal infection caused by *Botrytis cinerea* and 75% biocontrol activity against fungal infection caused by *Phytophthora infestans*. Control of fungal infections was also provided by the 10-fold diluted product against fungal infections caused by Pyricularia oryzae (75% protection), Septoria nodorum (90% protection), and *Puccinia recondita* (65% protection).

6.5. Production and Activity of Antimicrobial Preparations of Burkholderia casidae Strain 2.2N

6.5.1. Production of Antimicrobial Preparations

A culture of Burkholderia casidae strain 2.2N, grown as described above (Section 6.2.1), was centrifuged (5,000×G for 30 min at 4° C.), and the supernatant liquid collected. Two volumes of 70% (v/v) isopropanol were added to the supernatant and the resultant solution boiled for 1 minute. The solution was cooled to room temperature, then centrifuged (5,000×G for 30 min at room temperature), and the supernatant liquid collected. The solution was evaporated to the original culture volume in a rotary vacuum evaporator at 65° C. Talc (magnesium silicate) was added to the liquid at a ratio of 4 grams talc per 50 ml liquid. The suspension was stirred at room temperature for 30 min. The talc fraction was separated from the liquid by centrifugation (5,000×G for 30 min at room temperature). The talc fraction was collected and washed twice with distilled water employing centrifugation (5,000×G for 30 min at room temperature). The retained talc fraction was extracted with a 10-fold excess volume of 70% (v/v) isopropanol. The isopropanol-fraction, containing the eluted antimicrobial activity, was recovered by centrifugation (5,000×G for 30 min at room temperature). The isopropanol fraction was evaporated to dryness in a rotary vacuum evaporator at 65° C. and the antimicrobial preparations weighed. The antimicrobial preparations was dissolved in water to a concentration of 1 mg dry weight per ml prior to use in activity assays.

6.5.2. Activity of Antimicrobial Preparations

Antifungal activity of the antimicrobial preparation was assayed using procedures described in Section 6.2., above.

Ten microliter volumes of test material (cultures or antimicrobial preparations) were spotted on test plates overlaid with prey microorganisms and allowed to dry. Plates were incubated at room temperature and examined at hourly intervals for the appearance of zones of inhibition of microbial growth. Activity was measured as the diameter (mm) of the zones of inhibition of fungal growth.

As shown in Table 9, above, the antimicrobial preparation has antifungal activity.

6.6. Thermal Stability of Biocontrol Compositions

This section presents data on the thermostability of the various different inhibitory activities present in biocontrol compositions of the invention. A strain 2.2N culture was grown as described in Section 6.2.1 and used to prepare "Culture", "Filtrate" and "Fungicide" preparations as described in Section 6.2.2. Further, a portion of the supernatant, spent medium was treated with −70° C. acetone to final concentration of about 70% (v/v). The precipitated material was collected by centrifugation, dried, and dissolved in 8% (w/v) NaCl. This fraction was shown to have protease activity, and thus was designated the "Protease" preparation.

Each of these different preparations was treated for 15 min at temperatures ranging from 30° C. to 121° C. The biocontrol activity of untreated and heat-treated preparations was tested against *Saccharomyces cerevisiae* (anti-yeast activity), *Micrococcus luteus* and *Escherichia coli* (antibacterial activity), and *Aspergillus niger, Botrytis cinerea,* and *Septoria nodorum* (anti-filamentous fungi activity) following the procedures described in Section 6.2.4.

Table 17 shows that the "Protease" preparation, like the Culture preparation, contains at least three different biocontrol activities: anti-bacterial, anti-yeast and anti-filamentous fungi.

TABLE 17

Biocontrol Activity of Protease Preparation.

| Microorganism | Dia. of Zone of Inhibition | |
| --- | --- | --- |
|  | Culture | Protease |
| *Saccharomyces cerevisiae* | 20 mm | 17 mm |
| *Micrococcus luteus* | 23 mm | 12 mm |
| *Aspergillus niger* | 27 mm | 16 mm |
| *Escherichia coli* | ND[1] | 14 mm |
| *Septoria nodorum* | 22 mm | 14 mm |
| *Botrytis cinerea* | 33 mm | 13 mm |

[1]ND = Not determined.

Table 18 shows that the anti-yeast activity in all four preparations is highly heat-resistant. No significant loss of activity was encountered at heat treatment less than 121° C.

TABLE 18

Heat Stability of Activity Against *Saccharomyces cerevisiae*

| Temperature | Culture | Filtrate | Fungicide | Protease* | Comment |
| --- | --- | --- | --- | --- | --- |
| 30° C. | 17 mm | 9 mm | 16 mm | + | Control |
| 37° C. | 17 mm | 9 mm | 14 mm | + | |
| 50° C. | 17 mm | 9 mm | 14 mm | + | |

TABLE 18-continued

Heat Stability of Activity Against *Saccharomyces cerevisiae*

| Temperature | Culture | Filtrate | Fungicide | Protease* | Comment |
| --- | --- | --- | --- | --- | --- |
| 65° C. | 17 mm | 9 mm | 13 mm | + | |
| 80° C. | 16 mm | 9 mm | 10 mm | + | |
| 100° C. | 16 mm | 9 mm | 10 mm | + | |
| 121° C. | 3 mm | 9 mm | 10 mm | ± | Autoclave |

*Protease scored as presence or absence of zone of inhibition

Table 19 shows that Filtrate and Fungicide preparation contain no detectable antibacterial activity. Further, the activity present in the Culture and Protease preparations is relatively heat sensitive. That is, all activity was lost after incubating at 80° C. for 15 min.

TABLE 19

Heat Stability of Activity Against *Micrococcus luteus*

| Temperature | Culture | Filtrate | Fungicide | Protease* | Comment |
| --- | --- | --- | --- | --- | --- |
| 30° C. | 25 mm | 0 mm | 0 mm | + | Control |
| 37° C. | 25 mm | 0 mm | 0 mm | + | |
| 50° C. | 19 mm | 0 mm | 0 mm | + | |
| 65° C. | 18 mm | 0 mm | 0 mm | + | |
| 80° C. | 0 mm | 0 mm | 0 mm | 0 | |
| 100° C. | 0 mm | 0 mm | 0 mm | 0 | |
| 121° C. | 0 mm | 0 mm | 0 mm | 0 | Autoclave |

*Protease scored as presence or absence of zone of inhibition

Table 20 shows that the Filtrate preparation contains very little anti-filamentous fungi activity. Compared to the anti-yeast activity, the anti-filamentous fungi activity is more heat sensitive. Treatment at 100° C. for 15 min resulted in a significant loss of activity.

TABLE 20

Results: Heat Stability of Activity Against *Aspergillus niger*

| Temperature | Culture | Filtrate | Fungicide | Protease* | Comment |
| --- | --- | --- | --- | --- | --- |
| 30° C. | 28 mm | 6 mm | 13 mm | + | Control |
| 37° C. | 28 mm | 0 mm | 12 mm | + | |
| 50° C. | 26 mm | 0 mm | 12 mm | + | |
| 65° C. | 21 mm | 0 mm | 9 mm | + | |
| 80° C. | 18 mm | 0 mm | 10 mm | + | |
| 100° C. | 13 mm | 0 mm | 6 mm | + | |
| 121° C. | 0 mm | 0 mm | 0 mm | 0 | Autoclave |

*Protease scored as presence or absence of zone of inhibition

6.7. Anti-protozoan Activity of *Burkholderia casidae* Strain 2.2N

The experiment described below demonstrates that *Burkholderia casidae* strain 2.2N exhibits biocontrol activity against protozoa.

*Tetrahymena pyriformis* strain ATCC 30202 was grown in 10 ml of Tetrahymena medium number 357 at 25° C. to early-log phase in 18×150 mm tubes with rotation at 20 rpm. *B. casidae* strain 2.2 N was grown to mid-log phase in 10 ml TSM+S at 30° C. in a 125 ml Erlenmeyer flask with aeration by rotation at 60 rpm.

An aliquot of the mid-log *B. casidae* strain 2.2N culture was added to each of four duplicate *T. pyriformis* 10 ml cultures contained in 18×150 mm screw capped tubes. Cocultures and *B. casidae*-free cultures of *T. pyriformis* were incubated at 25° C. with 20 rpm.

Samples of the cultures and cocultures were removed periodically for cell count. The number of strain 2.2N cells in each coculture was measured by plating on TSM+S agar. The plates were incubated at 30° C. The number of strain 2.2N colonies appearing after a few days was counted in order to determine colony forming unit (CFU) of 2.2N per ml of coculture.

The number of *T. pyriformis* cells was determined by visually counting the number of cells in dilutions of coculture or culture using a microscope and a Petroff-Hauser counting chamber. The results are reported as cells per ml of coculture or culture.

Table 21 shows that coculturing led to an initial decline in the number of strain 2.2N cells within the first 12 hr of the coculture. At 27 hr after coculturing the number of strain 2.2N cells began to recover and continued to increase for the next 48 to 72 hours. By contrast, the number of *T. pyriformis* cells in the coculture increased continually for about 57 hr and then underwent a drastic reduction by 74 hr. No such reduction was observed for *T. pyriformis* cultured by itself. The precipitous drop in *T. pyriformis* cell number in the coculture indicates antagonism and possibly predation by strain 2.2N.

TABLE 21

Inhibition of growth of *Tetrahymena pyriformis* by B. casidae strain 2.2N.

| | T. pyriformis | | B. casidae |
|---|---|---|---|
| Length of Incubation | Control Cells/ml | Coculture Cells/ml | Coculture CFU/ml |
| 0 hr | $3.8 \times 10^5$ | $2.0 \times 10^5$ | $1.7 \times 10^8$ |
| 12 hours | $6.6 \times 10^5$ | $5.2 \times 10^5$ | $9.6 \times 10^6$ |
| 27 hours | $1.2 \times 10^6$ | $9.2 \times 10^5$ | $9.8 \times 10^7$ |
| 33 hours | $1.3 \times 10^6$ | $1.1 \times 10^6$ | $6.0 \times 10^7$ |
| 50 hours | $1.5 \times 10^6$ | $1.2 \times 10^6$ | $1.5 \times 10^8$ |
| 57 hours | $1.5 \times 10^6$ | $1.2 \times 10^6$ | $3.9 \times 10^8$ |
| 74 hours | $1.5 \times 10^6$ | $3.5 \times 10^4$ | $3.3 \times 10^9$ |
| 84 hours | $1.3 \times 10^6$ | $<2.0 \times 10^3$ | $3.3 \times 10^9$ |

Various publications are cited herein, the disclosures of which are incorporated by reference in their entireties.

The present invention is not to be limited in scope by the specific embodiments described herein. Indeed various modifications of the invention in addition to those described herein will become apparent to those skilled in the art from the foregoing description and accompanying figures. Such modifications are intended to fall within the scope of the appended claims.

What is claimed is:

1. A substantially pure culture or suspension of a bacterium Burkholderia casidae* or variant thereof, which *Burkholderia casidae* or variant exhibits biocontrol activity against a microorganism, and has a) a 16S rRNA gene comprising a sequence that is at least 97% similar to the sequence of SEQ ID NO:1 as determined by Clustal Analysis; and b) a cellular fatty acid composition comprising about 16% to about 20% C16:0 fatty acid, about 18% to about 22% C16:1 fatty acid, and about 35% to about 45% C18:1 (11,12) fatty acid;

wherein the microorganism is a bacterium, yeast, filamentous fungi, protozoan or algae.

2. The substantially pure culture or suspension of claim 1, which bacterium or variant thereof has a 16S rRNA gene comprising a sequence identical to that of SEQ ID NO:1; and a cellular fatty acid composition comprising about 18% C16:0 fatty acid, about 21% C16:1 fatty acid and about 39% C18:1 (11,12).

3. A substantially pure culture or suspension of *Burkholderia casidae* strain 2.2N having the accession number ATCC 55961, or a variant thereof.

4. The substantially pure culture or suspension of claim 1, 2 or 3, wherein the culture or suspension comprises at least 80% cysts.

5. The substantially pure culture or suspension of claim 1, 2 or 3, wherein the culture or suspension comprises at least 80% cells.

6. The substantially pure culture or suspension of claim 1, 2 or 3, wherein the *Burkholderia casidae* or variant thereof has been inactivated.

7. The substantially pure culture or suspension of claim 6, wherein the *Burkholderia casidae* or variant thereof has been inactivated by treating with heat or alcohol.

8. A cell-free filtrate or cell fraction prepared from the substantially pure culture or suspension of claim 1, 2 or 3.

9. A cell-free filtrate or cell fraction prepared from the substantially pure culture or suspension of claim 6.

10. An antimicrobial preparation comprising an alcohol-extract of a cell, cyst, culture, suspension, cell-free filtrate or cell fraction of a bacterium *Burkholderia casidae* or variant thereof, which *Burkholderia casidae* or variant exhibits biocontrol activity against a microorganism, and has a) a 16S rRNA gene comprising a sequence that is at least 97% similar to the sequence of SEQ ID NO:1 as determined by Clustal Analysis; and b) a cellular fatty acid composition comprising about 16% to about 20% C16:0 fatty acid, about 18% to about 22% C16:1 fatty acid, and about 35% to about 45% C18:1 (11,12) fatty acid;

wherein the microorganism is a bacterium, yeast, filamentous fungi, protozoan or algae.

11. The antimicrobial preparation of claim 10, wherein the bacterium or variant thereof has a 16S rRNA gene comprising a sequence identical to that of SEQ ID NO:1; and a cellular fatty acid composition comprising about 18% C16:0 fatty acid, about 21% C16:1 fatty acid, and about 39% C18:1 (11,12).

12. The antimicrobial preparation of claim 11, wherein the bacterium is *Burkholderia casidae* strain 2.2N having the accession number ATCC 55961, or a variant thereof.

13. The antimicrobial preparation of claim 10, 11 or 12, wherein the cell, cyst, culture, suspension, cell-free filtrate or cell fraction of *Burkholderia casidae* or variant has been inactivated of any live bacterium.

14. The antimicrobial preparation of claim 10, 11 or 12, wherein the alcohol-extract is prepared according to a method comprising:

a) boiling an alcoholic mixture comprising the cell, culture, suspension, cell-free filtrate or cell fraction and an alcohol;

b) clarifying the boiled mixture;

c) mixing the boiled mixture with magnesium silicate;

d) collecting the magnesium silicate;

e) washing the magnesium silicate with water; and f) eluting antifungal compounds from the magnesium silicate with an alcoholic solution, thereby producing the alcohol-extract.

15. A biocontrol composition comprising the substantially pure culture or suspension of claim 1, 2 or 3.

16. A biocontrol composition comprising the substantially pure culture or suspension of claim 4.

17. A biocontrol composition comprising the substantially pure culture or suspension of claim 5.

18. A biocontrol composition comprising the substantially pure culture or suspension of claim 6.

19. A biocontrol composition comprising the substantially pure culture or suspension of claim 7.

20. A biocontrol composition comprising sprayed-dried or freeze-dried cells of the substantially pure culture or suspension of claim 1, 2 or 3.

21. A biocontrol composition comprising sprayed-dried or freeze-dried cells of the substantially pure culture or suspension of claim 4.

22. A biocontrol composition comprising sprayed-dried or freeze-dried cells of the substantially pure culture or suspension of claim 5.

23. A biocontrol composition comprising sprayed-dried or freeze-dried cells of the substantially pure culture or suspension of claim 6.

24. A biocontrol composition comprising sprayed-dried or freeze-dried cells of the substantially pure culture or suspension of claim 7.

25. A biocontrol composition comprising the cell-free filtrate or cell fraction of claim 8.

26. A biocontrol composition comprising the cell-free filtrate or cell fraction of claim 9.

27. A biocontrol composition comprising the antimicrobial preparation of claim 10.

28. A biocontrol composition comprising the antimicrobial preparation of claim 11.

29. A biocontrol composition comprising the antimicrobial preparation of claim 12.

30. A biocontrol composition comprising the antimicrobial preparation of claim 13.

31. A biocontrol composition comprising the antimicrobial preparation of claim 14.

32. A method for producing an antimicrobial preparation from *Burkholderia casidae* or variant thereof, comprising:

a) boiling an alcoholic mixture comprising a cell, culture, suspension, cell-free filtrate or cell fraction of *Burkholderia casidae* or variant thereof, and an alcohol;

b) clarifying the boiled mixture;

c) mixing the boiled mixture with magnesium silicate;

d) collecting the magnesium silicate;

e) washing the magnesium silicate with water; and f) eluting antifungal compounds from the magnesium silicate with an alcoholic solution, thereby producing the antimicrobial preparation.

33. A method for isolating a *Burkholderia casidae* or variant thereof, which comprises (a) determining the 16S rRNA sequence and the cellular fatty acid composition of a predator bacterium which exhibits biocontrol activity against a microorganism; and (b) identifying a bacterium having (i) a 16S rRNA gene comprising a sequence that is at least 97% similar to the sequence of SEQ ID NO:1 as determined by Clustal Analysis, and (ii) a cellular fatty acid composition comprising about 16% to about 20% C16:0 fatty acid, about 18% to about 22% C16:1 fatty acid, and about 35% to about 45% C 18:1 (11,12) fatty acid;

thereby isolating the *Burkholderia casidae* or variant thereof.

34. The method of claim 33, wherein the bacterium has (i) a 16S rRNA gene comprising a sequence that is identical to the sequence of SEQ ID NO:1, and (ii) a cellular fatty acid composition comprising about 18% C16:0 fatty acid, about 21% C16:1 fatty acid and about 39% C18:1 (11,12).

\* \* \* \* \*